United States Patent
Sepetka et al.

[11] Patent Number: 6,022,340
[45] Date of Patent: Feb. 8, 2000

[54] BALLON/DELIVERY CATHETER ASSEMBLY WITH ADJUSTABLE BALLOON POSITIONING

[75] Inventors: Ivan Sepetka, Los Altos; Erik T. Engelson, Menlo Park, both of Calif.

[73] Assignee: Target Therapeutics Inc., Fremont, Calif.

[21] Appl. No.: 09/096,750

[22] Filed: Jun. 12, 1998

Related U.S. Application Data

[62] Division of application No. 08/566,606, Dec. 4, 1995, Pat. No. 5,882,334.

[51] Int. Cl.[7] .................................................. A61M 31/00
[52] U.S. Cl. ............................................ 604/500; 604/48
[58] Field of Search .............................. 604/49, 52, 53, 604/54, 96, 280, 101, 500, 48; 606/194; 600/434

[56] References Cited

U.S. PATENT DOCUMENTS

| | | |
|---|---|---|
| 4,739,768 | 4/1988 | Engleson . |
| 4,813,934 | 3/1989 | Engelson et al. . |
| 4,824,435 | 4/1989 | Giesy et al. . |
| 4,881,547 | 11/1989 | Danforth . |
| 4,909,252 | 3/1990 | Goldberger . |
| 4,983,166 | 1/1991 | Yamawaki . |
| 4,994,069 | 2/1991 | Ritchart et al. . |
| 5,024,658 | 6/1991 | Kozlov et al. . |
| 5,102,390 | 4/1992 | Crittenden et al. .................. 604/96 |
| 5,108,370 | 4/1992 | Walinsky . |
| 5,122,136 | 6/1992 | Guglielmi et al. . |
| 5,147,299 | 9/1992 | Mendoza et al. .................. 604/96 |
| 5,171,221 | 12/1992 | Samson . |
| 5,226,911 | 7/1993 | Chee et al. . |
| 5,232,445 | 8/1993 | Bonzel . |
| 5,250,071 | 10/1993 | Palermo . |
| 5,257,974 | 11/1993 | Cox . |
| 5,261,916 | 11/1993 | Engelson . |
| 5,304,198 | 4/1994 | Samson . |
| 5,320,605 | 6/1994 | Sahota . |
| 5,330,499 | 7/1994 | Kanesaka . |
| 5,336,205 | 8/1994 | Zenzen et al. . |
| 5,338,300 | 8/1994 | Cox ........................................... 604/96 |
| 5,368,567 | 11/1994 | Lee . |
| 5,388,590 | 2/1995 | Horrigan et al. . |
| 5,413,581 | 5/1995 | Goy . |
| 5,415,636 | 5/1995 | Forman . |
| 5,437,635 | 8/1995 | Engleson . |
| 5,536,250 | 7/1996 | Klein et al. . |
| 5,545,135 | 8/1996 | Iacob et al. . |
| 5,578,009 | 11/1996 | Kraus et al. ............................ 604/96 |
| 5,702,417 | 12/1997 | Hermann ................................ 606/194 |

FOREIGN PATENT DOCUMENTS 7-57246   6/1995   Japan .

OTHER PUBLICATIONS

Mandai et al., "Direct thrombosis of aneurysms with cellulose acetate polymer (Part I: Results of thrombosis in experimental aneurysms)" *J. Neurosurg.* (1992) 77:497–500.

Sugawara et al., "Experimental Investigations Concerning a New Liquid Embolization Method: Combined Administration of Ethanol–estrogen and Polyvinyl Acetate" *Neurol. Med. Chir.* Tokyo (1993) 33:71–76.

Takahashi et al., "Nonsurgical Treatment of AVM: Development of New Liquid Embolization Method" *Advances in Surgery for Cerebral Stroke,* Suzuki J. ed. Tokyo, Japan, Springer–Verlag (1988) pp. 215–224.

Taki et al., "A New Liquid Material for Embolization of Arteriovenous Malformations" *AJNR* (1990). 11:163–168.

*Primary Examiner*—Corrine McDermott
*Assistant Examiner*—Chris L. Rodriguez
*Attorney, Agent, or Firm*—Morrison & Foerster LLP

[57] ABSTRACT

This is a catheter assembly having an expandable balloon adjustably positionable over a polymeric delivery catheter shaft.

14 Claims, 9 Drawing Sheets

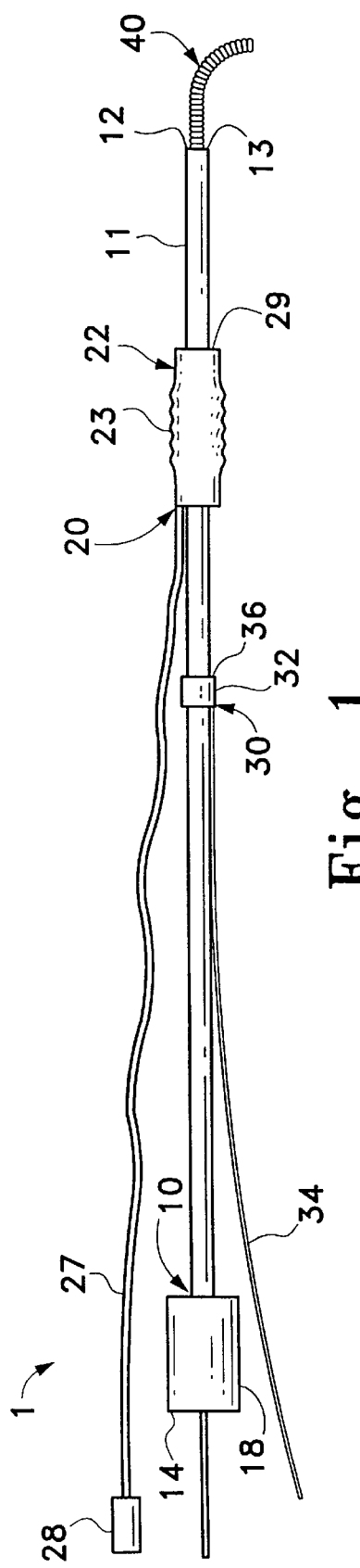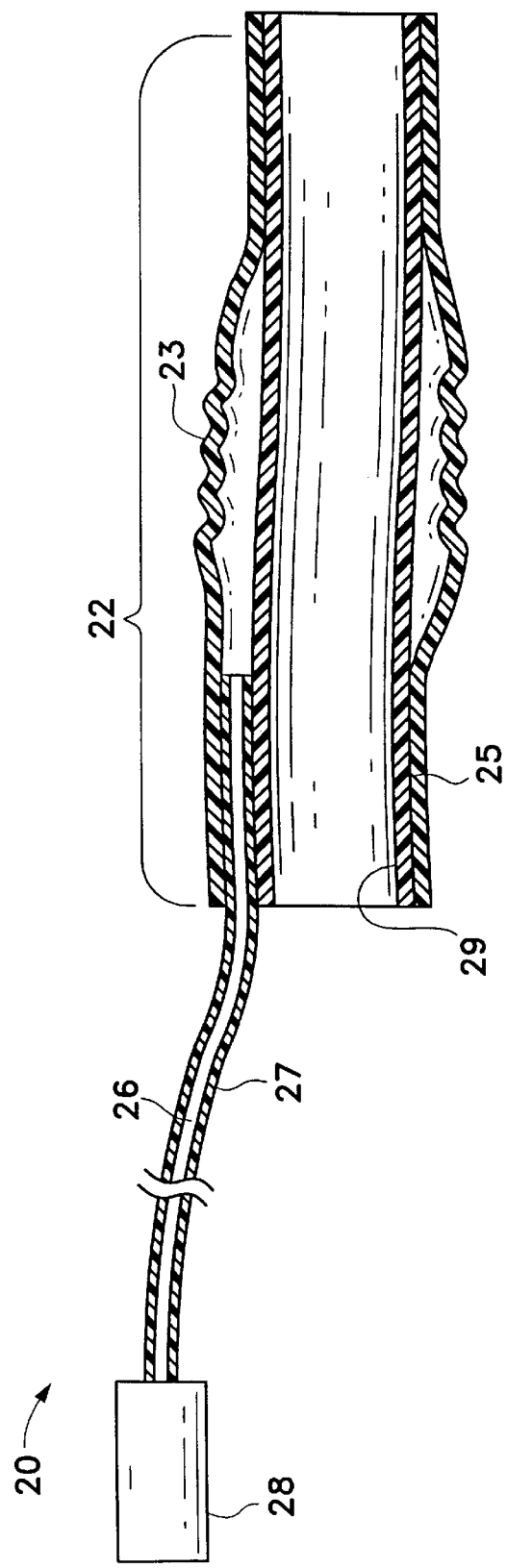

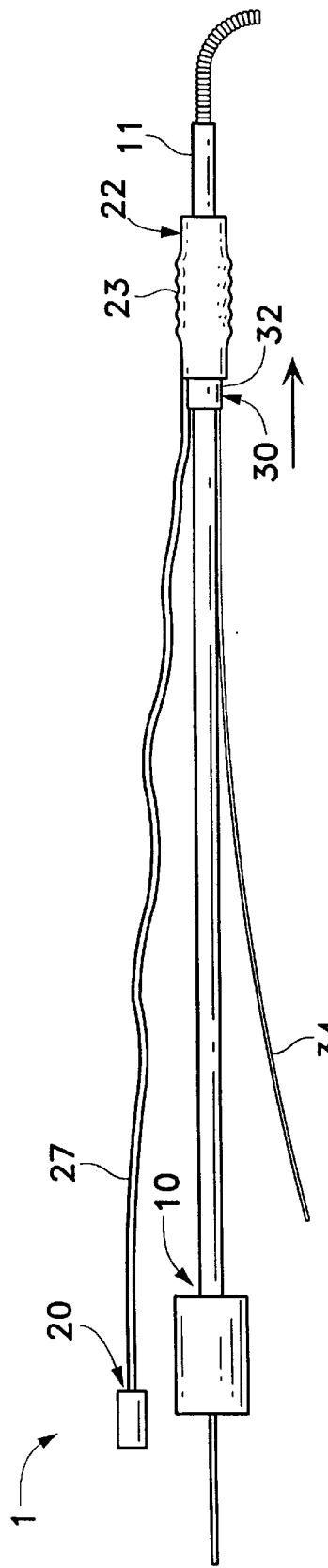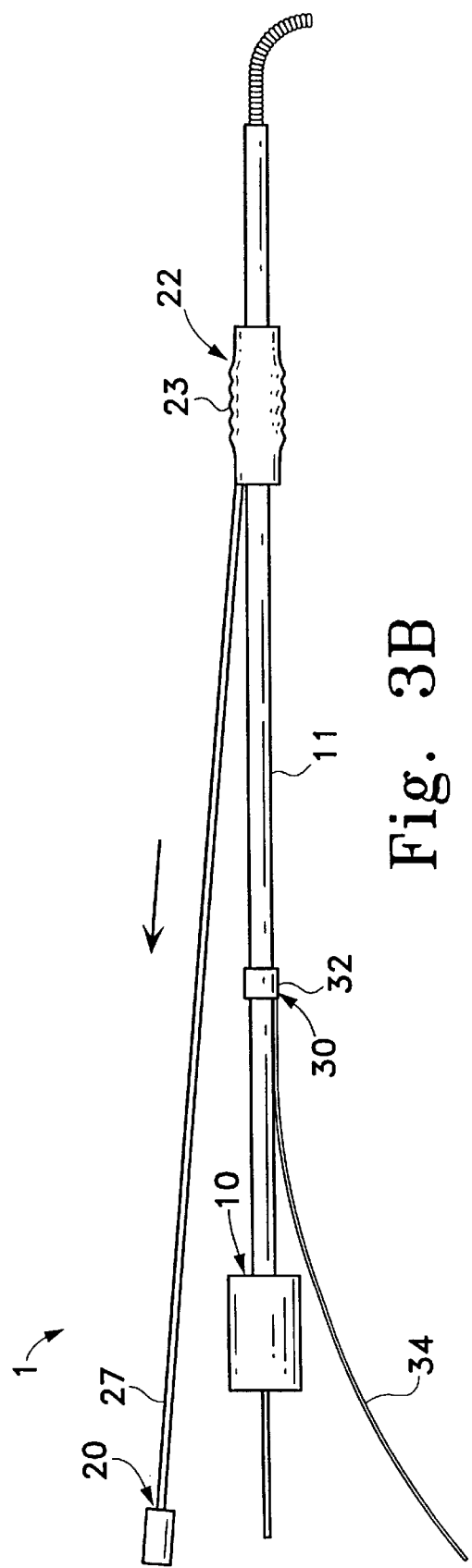
Fig. 3A
Fig. 3B

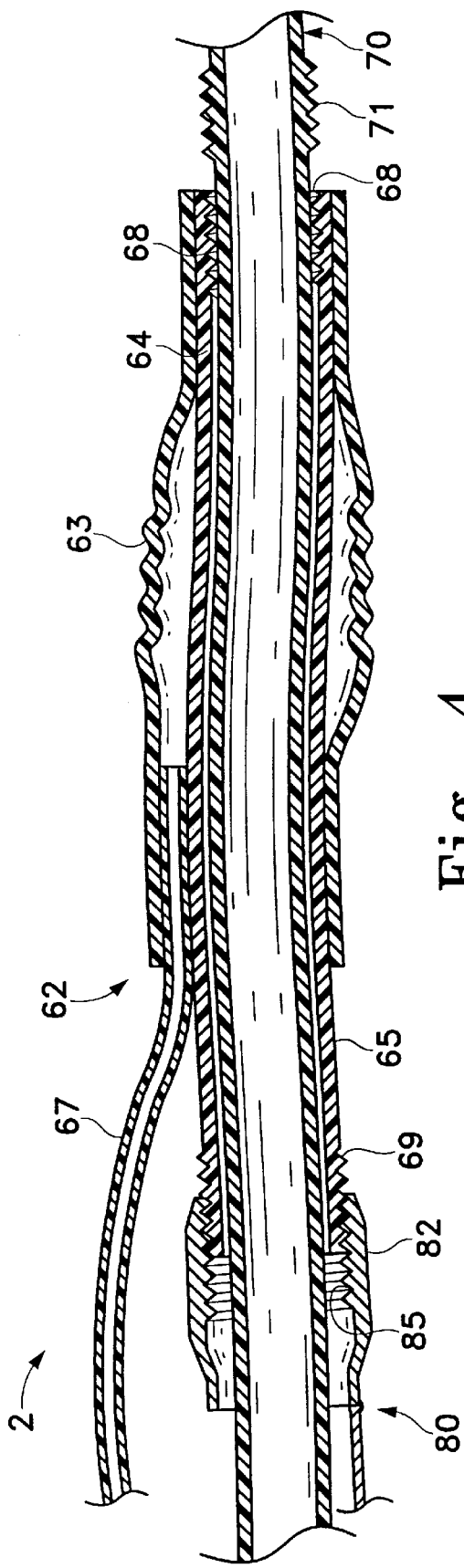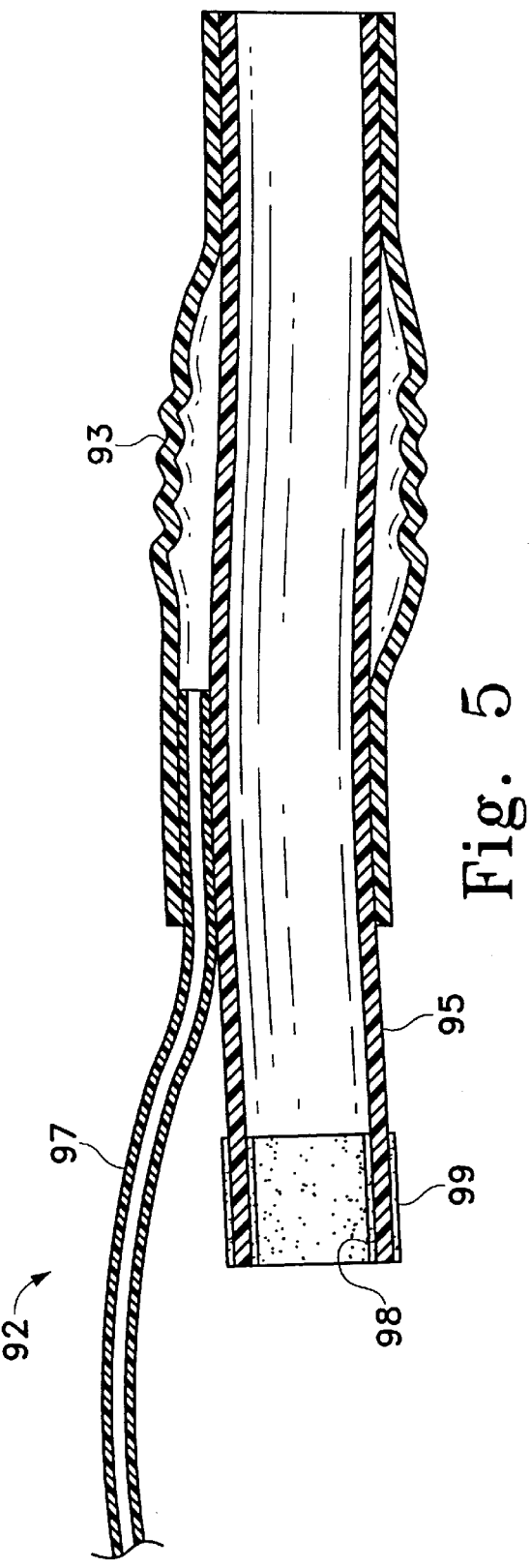

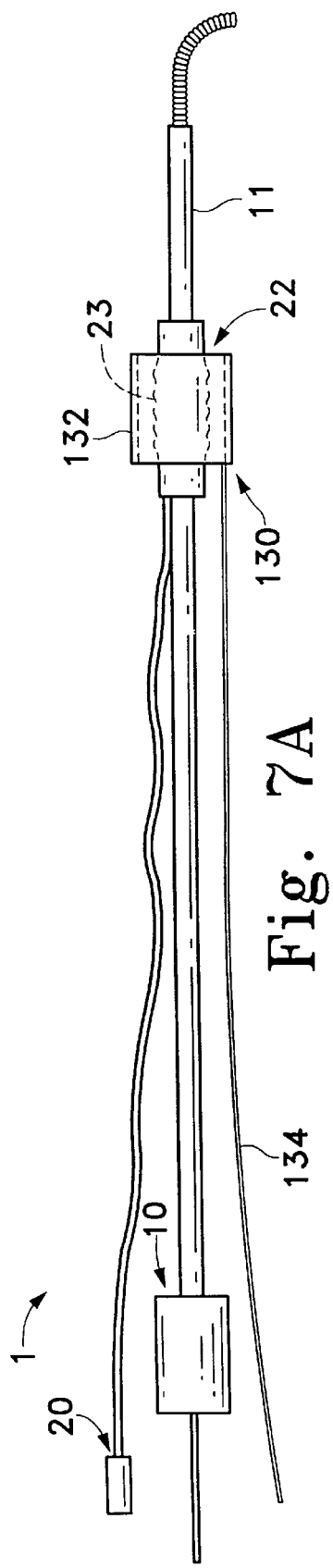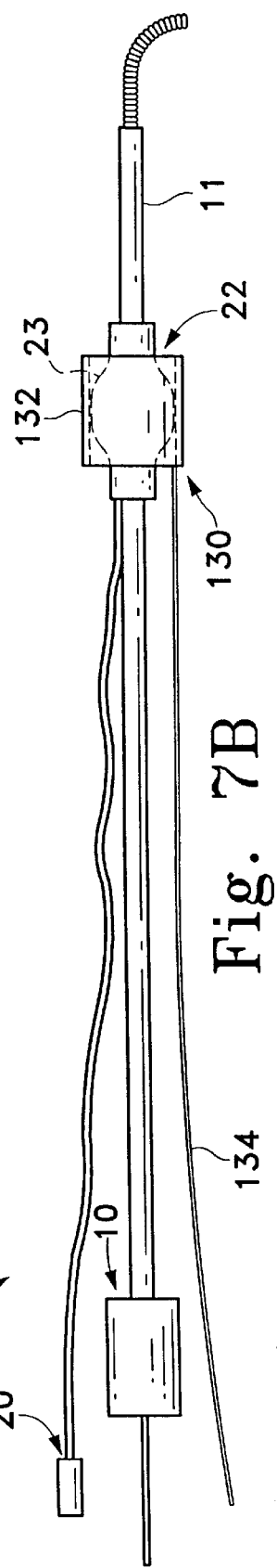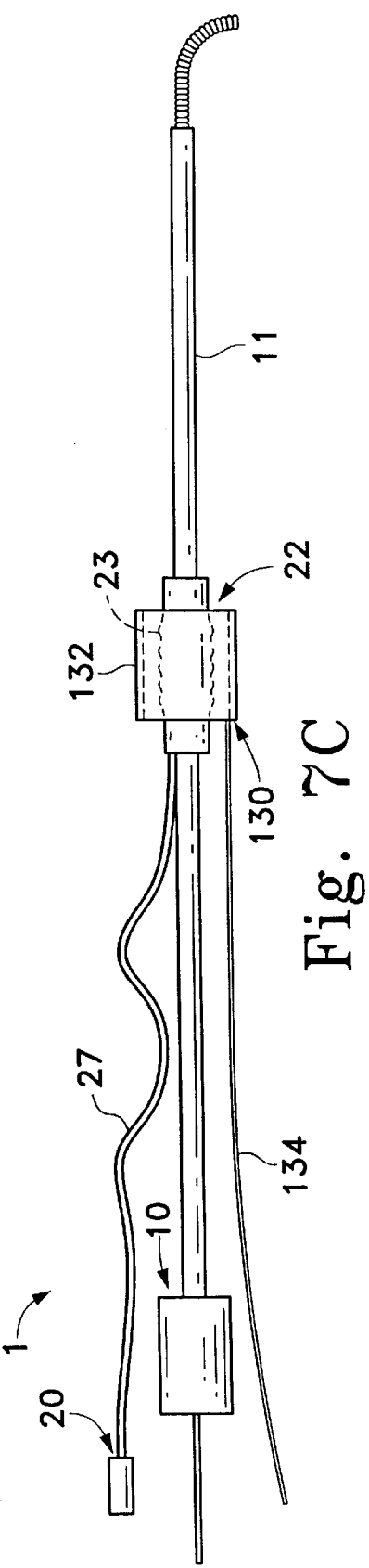

BALLON/DELIVERY CATHETER ASSEMBLY WITH ADJUSTABLE BALLOON POSITIONING

This application is a divisional application of application Ser. No. 08/566,606, filed Dec. 4, 1995, which issued on Mar. 16, 1999 as U.S. Pat. No. 5,882,334.

FIELD OF THE INVENTION

This invention is a medical device. More specifically, it is a catheter assembly having an expandable balloon adjustably positionable over a polymeric delivery catheter shaft.

BACKGROUND OF THE INVENTION

Percutaneous catheterization is a type of medical treatment that is generally less-invasive than directly accessing an internal body site for treatment, such as when using general surgery methods. In catheterization techniques, a long tubular catheter is introduced into the body through a puncture site. It is then passed to that site, usually through passageways such as the vascular tree. Treatment or diagnostic procedures may then be accomplished using the catheter by manipulation of the portion of the catheter remaining outside the body.

This invention involves a two-part catheter assembly—the first portion is an external balloon which is positioned over and is slideable or movable over the second portion: an internal catheter shaft.

Other medical devices to be compared to this invention include balloon catheters, delivery catheters, and balloon/delivery catheter assemblies.

BALLOON CATHETERS

Balloon catheters are medical devices that are used to facilitate various percutaneous medical treatments such as pressure monitoring, cardiac output and flow monitoring, angioplasty, artificial vaso-occlusion, and cardiac support. Balloon catheters generally have an elongated shaft with a fluid expandable balloon on the distal end and a coupler on the proximal end. These catheters generally include a lumen that extends from the coupler end to the balloon end and provide fluid to the balloon for its inflation.

One way that balloon catheters may be classified is by the way they are delivered into remote in-vivo sites. Among such balloon catheter categories are "flow-directed," "over-the-wire," "fixed-wire," and "single-lumen" balloon catheters.

"Flow-directed" balloon catheters are generally balloon catheters in which the balloon is inflated at a low pressure and acts like a sail in the blood stream. The inflated balloon, along with the attached catheter, is pulled downstream to a remote location by the blood flow acting on the inflated balloon.

"Over-the-wire" balloon catheters are generally balloon catheters that slideably track over an independent wire rail to a distally remote location. Generally, a radiopaque, steerable guide wire may be negotiated, via radiographic visualization, to a desired remote location such as a distal site in the vascular tree. Over-the-wire catheters generally have two lumens. A first lumen, the guide wire lumen, is used for slidably receiving and tracking over a steerable guide wire. The guide wire lumen often extends substantially the full length of the catheter and terminates at each end in open ports. Alternatively, the guide wire lumen may extend only between a distal port and a proximal port that is situated on the catheter distally of the catheter's proximal end. The second lumen is open at the distal end to a sealed, expandable balloon, and at the opposite proximal end to an open port. The proximal open end may be coupled with a pressurizable fluid source for inflating and deflating the balloon.

When a guide wire lumen extends the length of the catheter and the proximal port is accessible to a doctor during in-vivo use, the guide wire lumen may be used to exchange one wire for another. The balloon catheter is kept in place as a conduit delivery device during such guide wire exchanges—the wires do not need to be re-steered and tracked to the desired site each time. Also, this full length co-axial arrangement between catheter and wire allows manipulation of the wire's placement during the otherwise independent balloon inflation. This may be desirable, for instance, for seating the wire in a side vessel distal to the balloon inflation site to retain access thereto in the case the vasculature distal to the inflation site collapses as a result of the occlusion created by the balloon.

In contrast to the features just described, over-the-wire catheters may have a guide wire lumen extending only along a distal portion of the catheter length, with the proximal guide wire port located distally of the catheter proximal end. With this type of over-the-wire design, a shortened length of catheter rides co-axially on the wire. As such, a much shorter wire may be used—compared to full length co-axial over-the-wire designs. However, the proximal guide wire port in such designs is generally disposed within the body during in-vivo use. This often renders guide wire exchanges through the guide wire lumen quite difficult and often impossible while maintaining distal positioning of the catheter.

"Fixed-wire" balloon catheters have a steerable guide wire integrated into the balloon catheter assembly. In this way, the balloon catheter and guide wire may be advanced into distal anatomy as a unit. The guide wire may be torqued to cause a rotational response at the tip; although, in fixed wire catheters the guide wire is somewhat restrained in the limits of its movement such that it is not truly independent of the catheter. For example, the guide wire in a fixed wire balloon catheter usually may not be advanced or retracted axially and has a limit in the number of rotating turns that can be imparted to the wire relative to the catheter.

A single lumen may be provided in fixed wire balloon catheters, serving functions both as a balloon inflation lumen and a guide wire lumen. This provides a more modest profile when compared with multilumen catheter designs. In order to effectuate balloon inflation in a fixed wire balloon design having only a single lumen, the distal end of the balloon is sealed onto the wire. This may be accomplished either by affixing the balloon to the wire or by limiting the clearance between the wire and the balloon.

More recent balloon catheter designs are generally referred to as "single-lumen" catheters. Such single lumen catheters may include a guide wire that is independent of the catheter. The single lumen of "single lumen" catheters facilitates balloon inflation and at the same time is co-axial with the guide wire, as is the case in some "fixed-wire" designs. However, "single lumen" balloon catheters often have a valve mechanism provided on the catheter (or on the wire) such that a fluid seal may be selectively achieved between the wire and the catheter. The wire is slidable within the lumen and may be advanced and torqued relatively independently of the catheter in order to select and track to remote sites. Yet, the lumen may be tightly sealed onto the wire via the valve mechanism provided for balloon inflation when desired. Examples of balloon catheters that generally have one inflation lumen that is also coaxially disposed about a guide wire are disclosed in U.S. Pat. No. 4,813,934 to Engelson, et al. and U.S. Pat. No. 5,437,632 to Engelson, et al.

DELIVERY CATHETERS

In contrast to the balloon catheters described above, "delivery catheters" are generally characterized by an elongate polymeric tube having a lumen extending along their length with at least one distally disposed port for local delivery of therapeutic or diagnostic agents. Such agents may be fluids, such as drugs or radiopaque dyes, or devices, such as wires or vaso-occlusive coils. Delivery catheters may be designed to track over a wire or designed to follow a blood flow to a desired treatment site.

Some delivery catheters track over a wire to a desired site in a similar manner to "over-the-wire" catheters as described above. A steerable guide wire is extended to a point at or near the desired treatment site. The delivery catheter tracks over the wire so that it may be pushed at its proximal end and be advanced along the wire rail to the desired site. Thus, in "over-the-wire" delivery catheter designs, the catheter need not perform in the sub-selection and independent advancement into distal tortuous anatomy. The guide wire has that function. Rather, the over-the-wire delivery catheter design may be optimized for delivery of the agent. For instance, such a structure may result in the potential for a larger lumen diameter for a given delivery catheter diameter.

An alternative method of placing a delivery catheter at a remote site is by allowing blood flow, rather than a guide wire, to direct the delivery catheter through the branching anatomy to a remote site. Such a method is generally available when such a catheter possesses the appropriate distal flexibility and composition to be influenced in its direction by the forces of physiological flow.

Once any of these catheters is placed at the desired site, drugs or other agents may be delivered through a distal port. Agents may be so delivered either through the co-axial space between the catheter and the wire or through the open lumen with the wire removed. Alternatively or in addition to any end holes for such fluid or device delivery, "side hole" delivery catheters may have one or more ports near to the catheter distal end. These ports may be in fluid communication either with a single lumen or with more than one lumen. These multiple distal ports are often in a desired spatial arrangement, such as at a pre-determined spaced interval longitudinally along the catheter axis, in a spiral arrangement, etc.

One example of a delivery catheter that tracks over a guidewire and is used for end hole fluid delivery is disclosed in U.S. Pat. No. 4,739,768 to Engelson. Engelson discloses a catheter which can be guided over a guide wire along a tortuous path of at least about 5 cm through vessels of less than about 3 mm lumen inner diameter. Engelson further discloses delivery of fluid materials through a lumen provided after the guide wire is withdrawn. The fluid materials may include radiopaque agents, vaso-occlusive agents, and pharmacological agents.

One example of a delivery catheter that is flow directed to a distal site and is used for end hole delivery of agents is disclosed in U.S. Pat. No. 5,336,205 to Zenzen. Zenzen discloses an elongate tubular body comprised of a relatively stiff tapered proximal segment and a relatively flexible and strong distal segment that may be directed to the target site by means of blood flow to the site. Once at the site, diagnostic, therapeutic, or vaso-occlusive agents may be infused through a catheter lumen provided and into the target site.

Although flow-directed devices such as the delivery device disclosed in Zenzen are designed to allow physiological flow to provide desired distal placement, such flow may, in certain cases, direct the device away from a desired site. This may be the case where there is a bifurcated vascular tree wherein a disproportionate division of flow exists at a bifurcation in branching vessels. When there is a higher rate of flow into one branch than the other, a flow directed catheter may more than likely follow that flow into the first vessel. However, the second vessel with the lower flow contribution from the feeding vessel may actually be the desired site for the delivery catheter.

There is a need for a catheter assembly that allows for a flow directed catheter to be positioned beyond a bifurcation and into a branch of the feeding vessel that has inferior physiological flow to another branch at the bifurcation.

BALLOON/DELIVERY CATHETERS

Some medical conditions may require both a balloon catheter and a fluid delivery catheter to facilitate treatment. For instance, a patient may need a balloon inflation for performing angioplasty to re-open blocked vessels. Simultaneous or serial delivery of drugs such as thrombolytic agents, or of radiopaque dye for visualization, may be desirable at the angioplasty site. Or, a patient treatment may require fluid communication through a distal catheter port, which port may be desirably isolated from certain flow dynamics, such as from branching vessels other than a targeted vessel. For instance, such isolation may be desirable for drug delivery only into a targeted side branch vessel or for radiopaque dye delivery into that side branch.

In part to provide solutions to these needs, catheters have been disclosed having a fluid delivery port adjacent the balloon such that when the balloon is inflated against a vessel wall, the delivery site is isolated from hemodynamics opposite the balloon from the port. Such a port may be located distally of the balloon, for instance through a guide wire. Additionally, balloon catheters have been disclosed having lumens ending in side ports located proximally of the balloon. Balloon catheters of the types just described are herein referred to as "balloon/delivery" catheters, although particular references may use different terminology.

One example of a dilation-drug delivery catheter is disclosed in U.S. Pat. No. 5,415,636 to Forman. Forman describes a dilation-drug delivery catheter having a dilation portion for dilating a stenosis and a drug delivery portion for delivering antithrombolytic, antiproliferative, or other medication to the dilation site. The drug delivery portion of the catheter is located within the dilation portion, which dilation portion can be retracted to reveal the drug delivery portion distal thereto after dilation. Occlusion balloons described in the reference are preferably provided on the drug delivery portion to isolate the dilation site during drug delivery. A dilatation lumen, a drug delivery lumen, a guide wire lumen, and an inflation lumen in an inner catheter shaft are provided in the catheter described.

Another example of a balloon catheter having a lumen connected to a port proximal of a balloon is disclosed in U.S. Pat. No. 5,413,581 to Goy. Goy discloses a balloon dilatation catheter having a first lumen extending along the entire length of a shaft, which lumen is connected to a pump and, at the distal end of the catheter, to the inside of the balloon.

Through this lumen also passes a support wire connected firmly to the catheter at the catheter's distal end. The catheter shaft has an additional lumen which opens outwards of the catheter via an opening behind the proximal end of the balloon. Goy discloses that a controllable guide wire can be introduced into this additional lumen via an attachment piece, and that a measuring apparatus or an apparatus for introducing a contrast medium or drug can as well be connected to this additional lumen.

Another dilatation balloon catheter having an infusion lumen is found in U.S. Pat. No. 5,368,567 to Lee. Lee discloses a dilatation catheter having two or more associated fluid carrying tubes, the operative or distal end of one of which supplies fluid to inflate an expansible balloon. The operable or distal end of the other tube supplies an injectable dye or contrast enhancing fluid adjacent the proximal end of the balloon. The catheter embodiments disclosed by Lee also include a guide wire lumen separate from the balloon inflation lumen. The proximal end of the short guide wire lumen preferably begins adjacent the distal opening of a hollow tube lumen for injecting contrast medium proximal of the balloon. The distal end of the short guide wire lumen terminates distally of the sealed balloon.

U.S. Pat. No. 4,983,166 to Yamawaki discloses a balloon catheter having a balloon and a main passage ending in an opening behind the balloon. The reference discloses that, with the balloon inflated, drugs may be delivered through the opening and into other branches than that in which the balloon catheter tip is placed. Yamawaki discloses use of a circulatory curved tip end portion of the balloon catheter for inserting the catheter from a wider artery into a narrower artery diverging from the wider artery at an acute angle. The reference further discloses that a guidewire may be placed in the drug delivery passageway and out the opening behind the balloon, but does not otherwise disclose a guidewire lumen for tracking of the catheter over a guidewire to a remote in-vivo location.

One example of a medical treatment that has, for certain applications, been facilitated by delivery of therapeutic treatments through balloon/delivery catheters is artificial vaso-occlusion. Artificial vaso-occlusion or embolization is a medical treatment that often involves locally delivering a vaso-occlusive agent to a desired site. The agent therein causes a physiological occlusive response to flow or otherwise blocks or fills a body space. Different sites in the body where vaso-occlusion treatments have been used include aneurysms, blood vessels, and arteriovenous malformations.

Examples of various chemicals that have been used for in-vivo artificial vaso-occlusion include ethanol, estrogen, polyvinyl acetate ("PVA"), ethylene vinyl alcohol ("EVAL"), cellulose acetate polymer, or combinations thereof. Known delivery techniques for such vaso-occlusive agents include delivery through microcatheter-type delivery catheters, and delivery through balloon/delivery catheters having delivery ports adjacent to expandable balloons.

Accurate placement during the delivery of vaso-occlusive agents is critical, since inaccurate placement of the occlusive device or agent may undesirably occlude regions where continued flow must or should be maintained. Appropriate placement is especially important where an agent is relatively fluid and may migrate from the desired site if exposed to physiological flow. Therefore it is often desirable to isolate target delivery sites from flow into or from adjacent vasculature.

One reference to arterial embolization through a balloon catheter with a passage ending in an opening proximal of the balloon is in U.S. Pat. No. 4,983,166 to Yamawaki (introduced above). Yamawaki discloses use of a circulatory curved tip on the balloon catheter for subselecting of side branches.

Another example of an embolization treatment via balloon catheter delivery of chemical embolizing agents in the renal arteries is disclosed in "Nonsurgical Treatment of AVM: Development of New Liquid Embolization Method," Takahashi, et al., Suzuki J., ed., Advances in surgery for cerebral stroke, Tokyo, Japan: Springer-Verlag 1988:215–224. Takahashi discloses percutaneous delivery of conjugated estrogen diluted in 25% ethanol and polyvinyl acetate ("PVac"). According to the disclosure, PVac, when diluted in alcohol, becomes gelatinous in one second upon contacting water. Disclosed treatment methods included injections of PVac during proximal occlusion using slow leaking double lumen balloon catheters after 20 minute infusion of alcohol.

Other documents that disclose balloon catheter aided chemical delivery techniques for artificial vaso-occlusion include: "Experimental Investigations Concerning a New Liquid Embolization Method: Combined Administration of Ethanol-estrogen and Polyvinyl Acetate" by Sugawara, et al., Neurol Med Chir (Tokyo) 33,71–76, 1993; "A New Liquid Material for Embolization of Arteriovenous Malformations" by Taki, et al., AJNR 11:163–168, January/February 1990; "Direct thrombosis of aneurysms with cellulose acetate polymer (Part I: Results of thrombosis in experimental aneurysms)" by Mandai, M. D., et al., J Neurosurg 77;497–500, 1992.

These balloon/delivery catheter references disclose vaso-occlusive fluid delivery through a delivery catheter port, together with isolation of a vascular site by means of an expandable balloon integrated with the delivery catheter. However, vasculatures and disease/injury states vary among patients. The desired spatial arrangement of an occlusive balloon and a delivery port may vary accordingly for a given vaso-occlusion procedure. There is a need for a device assembly that allows for adjustable positioning of an occlusive balloon relative to a delivery port of a delivery catheter.

In addition to delivery of fluids for vaso-occlusion, a more recent artificial vaso-occlusion technique involves the delivery of implantable devices, particularly vaso-occlusive coils, to the desired site of occlusion. Such coils generally are made of a metal or metal alloy and may have various primary and secondary winds and dimensions. One of the benefits of using vaso-occlusive coils over other techniques is that a natural expansion of the coil diameter or other mechanical mechanism may be imparted to the coil such that it readily anchors itself against the walls of the delivery site. This may occur, for example, upon deployment of the coil from a restrained, stretched state within a catheter lumen and into a less constraining body space such that the coil's geometry passively transforms back to its relaxed, unrestrained memory state—or at least until it encounters a vessel wall against which it exerts a force to complete the anchoring process.

Various types of vaso-occlusion coils and delivery devices or systems have been disclosed, including coils having varying flexibilities and secondary geometries. Examples of such coils may be found in pending U.S. Patent Applications having the following Ser. Nos.: 08/413,970, filed Mar. 30, 1995; Ser. No. 29/037,001, filed Mar. 31, 1995; and Ser. No. 08/480,042, filed Jun. 6, 1995. Additionally, vaso-occlusive coils having vaso-occlusive fibers attached thereto have also been described (see for example U.S. Pat. No. 5,226,911 to Chee, et al.). Also, a novel vaso-occlusion coil adapted for use as a dielectric lead in a radio-frequency artificial vaso-occlusion system has been disclosed in pending U.S. patent application Ser. No. 08/497,507, filed Jun. 30, 1995.

In general, vaso-occlusive coils are delivered through microcatheters such as the type disclosed in U.S. Pat. No. 4,739,768 to Engelson (previously discussed). The microcatheter tracks a guide wire to a point just proximal of or within the desired site for occlusion. The coil is advanced through the microcatheter and out the distal end hole and is thereby implanted into the adjacent space. The mechanisms chosen for advancing the coil through and out of the delivery catheter and the resultant coil designs may vary. Coils that are mechanically detached from an integrated pusher after exiting a delivery catheter have been disclosed for example in U.S. Pat. No. 5,261,916 to Engelson, or U.S. Pat. No. 5,250,071 to Palermo. Similarly, electrically detachable coils have been disclosed for example in U.S. Pat. No. 5,122,136 to Guglielmi, et al. Pushable coils have also been disclosed, for instance in U.S. Pat. No. 4,994,069 to Ritchart, et al. Additionally, pending U.S. patent application Ser. No. 08/413,970, filed Mar. 30, 1995 describes very soft and flexible coils which are flow-injectable through the delivery catheter using, e.g., saline solution.

Although each type of previously disclosed coil may have distinct benefits, there remain certain clinical challenges. For example, one such challenge is the occasional occurrence of a recoil phenomena at the distal end of a delivery catheter when a coil implant is discharged. This recoil phenomena may compromise the ability accurately to place the coil or coils where desired.

One artificial vaso-occlusion treatment where the recoil phenomena is particularly undesirable is during vaso-occlusive coil delivery into aneurysms, such as berry aneurysms, that are formed along blood vessel axes. These coils may be delivered to the aneurysm in the following manner. A microcatheter is steered into or adjacent the entrance of an aneurysm, aided by a steerable wire. The wire is then withdrawn from the microcatheter lumen and replaced by the vaso-occlusion coil. The vaso-occlusion coil is advanced through and out of the microcatheter, desirably being completely delivered into the aneurysm. Where recoil forces are experienced at the microcatheter tip, the tip may unseat from its positioning in the aneurysm. A portion of the coil might then trail out of the aneurysm entrance zone and into the feeding vessel. This may cause undesirable occlusive response in the good, feeding vessel. Also, there may be an increased risk that the blood flow may induce movement of the coil farther out of the aneurysm, resulting in a more developed embolus in the good vessel.

Although catheter distal tip shapes may be formed on delivery microcatheters to help support the distal tip during deployment of vaso-occlusive agents, this may in some circumstances provide only a partial solution. There is a need for a delivery catheter assembly that prevents or minimizes delivery catheter recoil during delivery of vaso-occlusive agents.

None of the cited references disclose a balloon/delivery catheter assembly having a balloon catheter with an expandable balloon that is variably positionable along the polymeric delivery shaft of an over-the-wire or flow-directable delivery catheter.

Nor do these references disclose a balloon/delivery catheter assembly that includes a single-lumen balloon catheter having a polymeric delivery catheter shaft coaxially disposed within the inflation lumen thereof, such coaxial arrangement providing a tightly toleranced distal fluid seal region that allows for controllably sustained balloon inflation.

Nor do these references disclose a balloon/delivery catheter assembly that allows for a balloon to be advanced over and distally beyond a flow-directable catheter in a first branch of a bifurcation, such that subsequent inflation of the balloon diverts flow into a second branch of the bifurcation sufficient to reposition the flow-directed catheter into the second branch.

Nor do these references disclose a balloon/delivery catheter assembly that minimizes recoil to the delivery catheter during delivery of agents through a delivery catheter port by allowing variable positioning and inflating of a balloon at a chosen location along a delivery catheter shaft.

SUMMARY OF THE INVENTION

This invention is a catheter assembly in which a balloon of a balloon catheter is variably positionable along the polymeric delivery shaft of a delivery catheter. The balloon catheter of the assembly may have an inflation coupler, a distal balloon catheter end portion with an expandable balloon fluidly coupled to the inflation coupler, and a balloon catheter lumen extending between first and second generally collinear ports. The delivery catheter of the assembly has a polymeric delivery shaft with a delivery lumen extending between a proximal delivery port and a distal delivery port. The distal balloon catheter end portion is coaxially positionable along at least a portion of the polymeric delivery shaft.

In one balloon catheter embodiment of the assembly described, the inflation shaft has a longitudinal axis different than the polymeric delivery catheter shaft. In an alternative balloon catheter embodiment, the inflation shaft and distal balloon catheter end portion are both coaxially disposed about the polymeric delivery shaft. Preferable to this embodiment, the balloon catheter lumen forms a fluid coupling between the inflation coupler (as needed) and the expandable balloon. Further, there may be a valve seat in a distal balloon tip region that has a tight coaxially clearance about an outer surface of the polymeric delivery shaft. This valve seat clearance forms a slideable interference fit that provides a controlled fluid seal so that the balloon may be pressurized for inflation.

In another embodiment, the distal balloon catheter end portion is adapted to be positioned on the polymeric delivery shaft at a chosen location with a friction fit between the balloon catheter lumen and the polymeric delivery shaft. Alternatively, an inner surface of a balloon catheter lumen and an outer surface of the delivery catheter may be threaded so that the balloon may be positioned on the polymeric delivery shaft by rotating a threaded coupling formed by the two surfaces.

In a further embodiment, a positioner may be provided that is adapted to slide coaxially over the polymeric delivery shaft and to transmit forces from a user to the distal balloon catheter end portion. Such forces may be push, pull, or torsional forces.

Also contemplated are preferred methods of using the embodiments described. The balloon may be desirably placed at a chosen position along the delivery catheter and then the assembly can be introduced into the body. Alternatively, the delivery catheter may be introduced into the body at the desired location, after which the balloon may be advanced over the delivery catheter to a desired position. In a further aspect of the invention, the balloon may be repositioned to a second position along the polymeric delivery shaft. This may be done by manually repositioning the balloon while the assembly is withdrawn, or by remotely using a positioner of the type described while the assembly remains within the body.

In one medical procedure, for instance, the balloon may be advanced across a lesion and then inflated. Or, the balloon may be placed in a branch vessel and inflated to occlude flow through that vessel. Such branch vessel occlusion may be desired so that a flow-directed catheter can then be flow-directed into a second vessel branch that otherwise would not be so placeable. Additionally, the balloon may be inflated to engage a vessel wall prior to delivery of an agent through a port of the delivery catheter. Such inflation may reform the distal end of the delivery catheter into a relatively fixed position against the vessel wall to resist delivery catheter recoil during delivery of vaso-occlusive agents or devices.

BRIEF DESCRIPTION OF THE DRAWINGS

FIG. 1 is a perspective view of one embodiment of the present invention, showing a balloon/delivery catheter assembly including a balloon catheter with a balloon coaxially disposed in a first chosen position along the polymeric delivery shaft of a delivery catheter, and also showing an optional positioner coaxial to the delivery catheter shaft and proximal of the balloon.

FIG. 2 shows a cut-away side view of one preferred balloon catheter design useful in the assembly of FIG. 1.

FIG. 3A is a perspective view of the assembly of FIG. 1, showing the distal balloon catheter end portion pushed distally by the positioner to a second chosen position.

FIG. 3B is a perspective view of the assembly of FIG. 1, showing the distal balloon catheter end portion pulled from the second position of FIG. 3A and back to the first position of FIG. 1 after tension is applied to the inflation shaft of the balloon catheter.

FIG. 4 shows a cut-away side view of another balloon/delivery catheter assembly embodiment of the invention, showing a threaded coupling between the inner surface of the balloon catheter and the outer surface of the delivery shaft.

FIG. 5 shows a cut-away side view of another distal balloon catheter end portion embodiment for use in the invention having frictional engagement between the distal balloon catheter end portion and a positioner cuff.

FIG. 7A is a perspective view of another embodiment, with the positioner lumen shown coaxially disposed about the balloon of the balloon catheter.

FIG. 7B shows a perspective view of the assembly of FIG. 7A with the balloon expanded within the positioner lumen to engage the positioner.

FIG. 7C shows a perspective view of the assembly of FIG. 7A after the positioner and balloon have been withdrawn from their position in FIG. 7A to a more proximal position relative to the delivery catheter tip, and showing the balloon deflated.

DETAILED DESCRIPTION OF THE INVENTION

Figure 6:
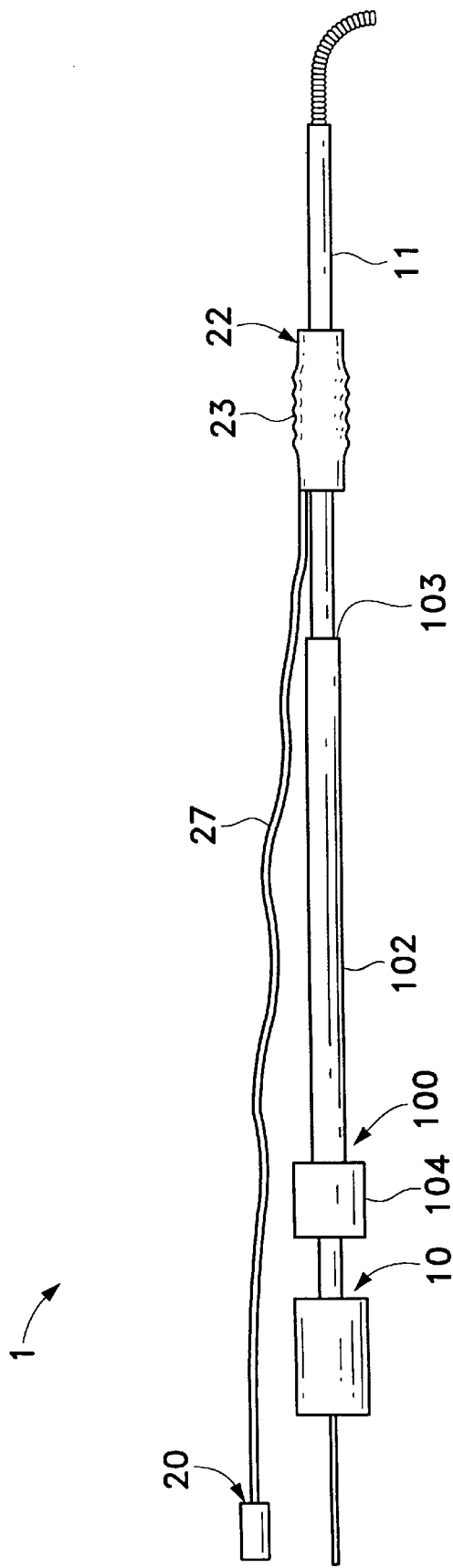
FIG. 6 shows a further embodiment of the current invention wherein the entire length of a positioner is coaxial with the polymeric delivery shaft.

One embodiment of the present invention is shown in FIG. 1, wherein a balloon/delivery catheter assembly 1 is shown to include delivery catheter 10 together with balloon catheter 20 which has a distal portion positioned coaxially to delivery catheter 10. Also shown with balloon/delivery catheter assembly 1 in FIG. 1 are positioner 30 and guidewire 40.

The design for delivery catheter 10 is shown in FIG. 1 to be an "over-the-wire" design, with a wire 40 shown extending both distally and proximally from lumen 12 of the delivery catheter 10. Delivery catheter 10 may also be a "flow-directed" catheter, as may be known in the art, wherein the guidewire as shown in FIG. 1 would not be necessary (or at most would be optional). In either case, such delivery catheter 10 generally has a polymeric delivery shaft 11, a delivery lumen 12 extending between distal end port 13 and proximal end port 14, and a proximal delivery catheter coupler 18.

Delivery catheter 10 may be made of polymeric material. Such polymeric construction may have differing materials between the proximal and distal regions of the polymeric delivery shaft. Such variations in material and design stiffness may be chosen depending on the particular intended use of the delivery catheter. In an "over-the-wire" delivery catheter design, a catheter such as that described in U.S. Pat. No. 4,739,768 to Engelson (introduced above) would be sufficient in the current assembly. In a "flow-directed" delivery catheter design, a catheter such as that described in U.S. Pat. No. 5,336,205 to Zenzen would suffice. The disclosures in these documents are incorporated in their entirety by reference.

The balloon catheter 20 shown in FIG. 1 has a distal balloon catheter end portion 22 with a balloon 23, an inflation shaft 27, and an inflation coupler 28.

The distal balloon catheter end portion 22 is shown in FIG. 2 to comprise an expandable balloon 23 that is sealed distally onto a guide member 25 and proximally over guide member 25 and inflation shaft 27. The proximal seal must be such that the inflation shaft 27 remains in fluid communication with the interior space of the balloon 23 so that it may serve as a fluid conduit for balloon expansion.

The balloon 23 may be of a compliant material, such as a material chosen from the group consisting of latex, silicone, or polyvinyl chloride. Such a soft, pliable material may be particularly preferred when the purpose of expanding the balloon 23 is simply to occlude a vessel from flow. Such material may also minimize vessel wall trauma when the balloon is inflated to provide a firm seal of the delivery catheter 10 against a vessel wall, such as to provide support against recoil when fluids or devices are ejected from a delivery port.

Alternatively, balloon 23 may be made of a less compliant, higher pressure material, such as a material chosen from such materials as polyethylene, nylon, polyolefin copolymer (POC), polyethylene terephthalate (PET), or polyimide. These materials may be particularly desirable if the purpose of balloon expansion in using this assembly is to dilate a constricted portion of a body passageway, such as a vessel or fallopian tube. When the balloon is of relatively non-compliant material, it is preferable that the balloon be longitudinally folded so to lower its profile during introduction into the body.

In one preferred construction of distal balloon catheter end portion 22, balloon 23 is made of latex or silicone rubber, the guide member 25 is made of polyethylene, and the inflation shaft 27 is made of a poly fluorocarbon such as TEFLON. In this construction, it is preferable to adhesively bond the balloon seals to the inner tubing. In alternative methods and constructions, the balloon seal regions may be heat melted onto the inner tubing, or may be adhesive or solvent bonded, depending upon the materials of choice for a particular application.

Inflation shaft 27 is shown in FIG. 1 and FIG. 2 extending proximally of distal balloon catheter end portion 22. Inflation shaft 27 has an inflation lumen 26 that provides for fluid communication between inflation coupler 28 and balloon 23. In the various embodiments of the current invention, providing this conduit lumen 26 for fluid communication is one of only two performance criteria that may be required of inflation shaft 27. In a second aspect, inflation shaft 27 may also be used to provide a tension member with which the distal balloon catheter end portion 22 may be pulled proximally to reposition balloon 23 along the polymeric delivery shaft 11.

Beyond serving as a conduit for balloon inflation and optionally as a member for balloon repositioning, there are no other restrictions on the design for inflation shaft 27 of this embodiment. Inflation shaft 27 may be made of more highly flexible material than in previous balloon catheter designs which require more structure in the proximal balloon catheter regions for manipulating the distal balloon catheter portions in-vivo. Inflation shaft 27 may also have a very low profile when compared to other balloon inflation shafts, since the lumen and wall dimensions that are required to achieve adequate inflation, and perhaps tensile strength, in this inventive assembly are much lower than would be required when push transmission is an additional required property.

Inflation shaft 27 allows for minimal if not negligible effect on the overall performance of the assembly. For instance, the low profile and flexible inflation shaft 27 contributes very little bending resistance to the assembly, and does not significantly degrade the trackability of the assembly when compared to the trackability of polymeric delivery shaft 11 when taken alone. This is so because the two members are independent of each other, out of coaxial arrangement, and the inflation shaft 27 alone is of so very low profile and flexibility. This same low profile design for the inflation shaft 27 allows for minimal passive flow resistance when the assembly is in-dwelling during use.

Thus, the coaxial distal balloon catheter end portion 22 may be the only portion of the balloon catheter 20 that has functional impact on the structural performance of the polymeric delivery shaft 11. And, the structural impact of this component may even still have minimal or negligible affect on the delivery catheter's pushability, trackability, or other assembly performance characteristics. This would especially be the case when the distal balloon catheter end portion 22, including balloon 23, is extremely short such that stiffness transitions along the delivery shaft 11 are minimized.

In use of the catheter assembly 1 shown in FIG. 1, it may be desirable to reposition the balloon 23 on distal balloon catheter end portion 22 from a first chosen position to a second chosen position along polymeric delivery shaft 11. One such way to reposition the balloon is to withdraw the assembly from the body and manually reposition the distal balloon catheter end portion 22. Alternatively, the balloon may be remotely repositioned with a positioner while the assembly remains disposed in-vivo.

One type of a positioner useful with the balloon/delivery catheter assembly of the invention, such as with assembly 1 of FIG. 1, is shown at positioner 30, also in FIG. 1. Positioner 30 comprises a positioner cuff 32 and a positioner shaft 34 extending proximally of the positioner cuff 32, shown in FIG. 1 as positioner wire 34. Positioner 30 is designed to be moveable over the polymeric delivery shaft 11, and to engage the distal balloon catheter end portion 22 to reposition that balloon end portion 22 along the polymeric delivery shaft 11. Consequently, the material of construction of the positioner 30 should be of sufficient rigidity to transmit "pushing" forces from the positioner wire 34 to the positioner cuff 32 and move the distal balloon end portion 22 distally.

Positioner cuff 32 has a positioner lumen 36 that allows positioner cuff 32 to ride coaxially over and along the polymeric delivery shaft 11. In FIG. 1, this coaxial positioner cuff 32 is positioned proximally of balloon catheter end portion 22. The geometric features and material construction of the positioner cuff 32 may be chosen depending upon the desired interface with the distal balloon catheter end portion 22 for engaging and repositioning that portion. Such positioner cuff features would also be chosen according to the preferred relation to the size and materials of the other components of the system (as well as considering the intended use in a particular application). For instance, when the polymeric delivery shaft 11 is of a certain outer diameter and material, there may be a preferred complementary inner diameter, length, and material for positioner cuff 32 to allow it to move along polymeric delivery shaft 11 efficiently during the intended use of the assembly. When such parameters for polymeric delivery shaft 11 change, so would the ideal complementary parameters of the positioner cuff 32.

However, one preferred design for positioner cuff 32 is a relatively short ring or band adapted to coaxially advance over the polymeric delivery shaft 11 without collapsing or binding the polymeric delivery shaft 11 when that shaft is positioned in the bending tortuosities of in-vivo vessels. Positioner cuff 32 may be made of metal, such as stainless steel, gold, platinum, tungsten, nickel-titanium alloys, or alloys of such metals. It is further preferable that such material construction for positioner cuff 32 be radiopaque so that its position along the polymeric delivery shaft 11 may be visualized relative to the distal balloon catheter end portion 22 via x-ray. One construction of the positioner cuff 32 that may be acceptable is a band constructed of such metals or alloys as described and having a length ranging from 1 mm to 5 mm.

Positioner wire 34 for positioner 30 is shown in FIG. 1 as a wire that extends proximally from positioner cuff 32 and externally of the body for user manipulation. Preferably, relatively stiff and durable metal is chosen for this core wire so that forces may be transmitted under manipulation without deformation of the material that might degrade performance of the wire. For example, stainless steel may be preferable for its high stiffness properties. Or, an alloy of nickel and titanium may be preferable for its stiffness properties together with a characteristically high elasticity when deformed. Positioner wire 34 may be assembled to positioner cuff 32 by a variety of methods, such as by welding or soldering, as may be apparent to one of ordinary skill.

FIGS. 3A and 3B show the assembly of FIG. 1 with the distal balloon catheter end portion 22 repositioned distally and proximally, respectively.

FIG. 3A shows the balloon/delivery catheter assembly 1 of FIG. 1 with the balloon 23 repositioned from a first position on polymeric delivery shaft 11 (shown in FIG. 1) to a second more distal position. In this view, positioner 30 is shown to have been advanced distally such that positioner cuff 32 is shown to abut a confronting end of distal balloon catheter end portion 22. Push forces applied to the positioner wire 34 translate along the wire to the positioner cuff 32 and onto the distal balloon catheter end portion 22 in the distal direction. The distal balloon catheter end portion 22 is thereby moved so that balloon 23 is repositioned from the first position in FIG. 1, distally along the polymeric delivery shaft 11, and to the second chosen position. Radiopaque markers, such as metallic markers, or materials may be provided on the distal balloon catheter end portion, on the delivery catheter, and on the positioner cuff according to conventional methods and in order to aid in accurate positioning during X-ray visualization.

FIG. 3B shows the balloon/delivery catheter assembly 1 of FIGS. 1 and 3A after the distal balloon catheter end portion 22 has been retracted to reposition balloon 23 from the second position of FIG. 3A and back to the first position of FIG. 1. Such proximally directed repositioning of the distal balloon catheter end portion 22 may be achieved in many ways, one of which is shown in FIG. 3B. FIG. 3B depicts the retraction of the balloon via pulling on the inflation shaft 27.

Although FIGS. 3A and 3B show repositioning of the distal balloon catheter end portion 22 by pushing it with positioner 30, and pulling it with inflation shaft 27, several alternative embodiments of the inventive assembly and/or methods may be employed to achieve the desired repositioning. Two such alternative embodiments are shown in FIG. 4.

FIG. 4 shows a distal balloon catheter end portion 62 that is similar to that shown in FIG. 2, however here showing balloon catheter lumen inner surface threads 68 located interiorly of balloon catheter lumen 64, and also showing guide member outer surface threads 69 located exteriorly on an extension of guide member 65. Distal balloon catheter end portion 62 is shown in FIG. 4 together with polymeric delivery catheter 70 to form balloon/delivery catheter assembly 2, which is further shown in FIG. 4 to be assembled together with positioner 80. As was the case with balloon assembly 23 in FIG. 2, guide member 65 forms the inner lumen of distal balloon catheter end portion 62 and is sealed with balloon 63 to form an inflatable balloon, which balloon is inflatable by inflation tubing 67.

The inner surface threads 68 shown in FIG. 4 are adapted with a handedness and dimension to threadedly couple with delivery shaft outer surface threads 71 of delivery catheter 70. In this assembly, distal balloon catheter end portion 62 is coaxially moved distally over the polymeric shaft of delivery catheter 70 such that balloon catheter lumen inner surface threads 68 come into contact with the delivery shaft outer surface threads 71. Subsequent rotation of one of the distal balloon catheter end portion 62 or the polymeric delivery catheter 70 induces threaded coupling between the two components. Further rotation advances distal balloon catheter end portion 62 along polymeric delivery catheter 70 as is controlled by their coupling. Only rotation as such may controllably advance the distal balloon catheter end portion 62 in the threaded coupling of this assembly. The threaded coupling prevents the coaxial "sliding" as would otherwise occur when push and pull forces are applied.

Balloon catheter lumen inner surface threads. 68 may be formed using a variety of methods. For example, such threads may be formed into the polymer of guide member 65, such as by heat shrinking or melting the polymer onto a threaded mandrel. Or, a separate threaded member, such as a metal band with interior threads may be provided interiorly of distal balloon catheter end portion. This type of threaded member may be bonded to the distal balloon catheter end portion such as by a melt bond, where a threaded polymeric member is provided, or by an adhesive bond. Similar construction may be provided, although inversely with exterior threading, for guide member outer surface threads 69 and for polymeric delivery shaft outer surface threads 71.

In using the assembly 2 of FIG. 4, initial positioning of the distal balloon catheter end portion 62 on polymeric delivery catheter 70 may be achieved by manually threadedly coupling the two components, as just described, prior to insertion of the assembly into the body. Subsequent repositioning of the balloon 63 may be achieved manually or with a positioner.

For manual repositioning of balloon 63 in FIG. 4, balloon/delivery catheter assembly 2 may be withdrawn from the body and repositioned with manual rotation of distal balloon catheter end portion 62 at the threaded coupling. Alternatively, a positioner such as positioner 80 shown in FIG. 4 may be used to reposition the distal balloon catheter end portion 62 along the threaded polymeric delivery catheter 70 while assembly 2 is in the body. In such case, the positioner and distal balloon catheter end portion must both be adapted such that their engagement allows for rotation of the positioner to induce rotation of the distal balloon catheter end portion.

One example of how a rotational adaption between positioner and distal balloon catheter end portion may be achieved is with a second threaded adaption between these components. FIG. 4 shows such a threaded coupling between guide member outer surface threads 69 and positioner inner surface threads 85, located interiorly of positioner cuff 82 of positioner 80. In this embodiment, positioner 80 may be advanced distally until the distally leading edge of positioner inner surface threads 85 confront the proximally leading edge of guiding member outer surface threads 69. Subsequent rotation of positioner 80 will threadedly couple the positioner 80 with distal balloon catheter end portion 62. This positioner/distal balloon catheter end portion coupling or engagement may be used with axial frictional repositioning of the balloon, such as was shown with assembly 1 in FIGS. 3A–3B (particularly where the distal balloon catheter end portion is adapted for frictional interface with the delivery catheter as in those figures). Or, in the case of a balloon/delivery assembly such as assembly 2 in FIG. 4, positioner inner surface threads 85 may reach a stop in the guide member outer surface threading. In that situation, continued rotation of the positioner 80 will impart rotation to distal balloon catheter end portion 62, such rotation achieving the desired repositioning along the engagement between delivery shaft outer surface threads 71 and positioner inner surface threads 85.

A further embodiment for a distal balloon catheter end portion for use in an assembly similar to balloon/delivery catheter assembly 1 in FIG. 1 or balloon/delivery catheter assembly 2 in FIG. 4 is shown in FIG. 5. FIG. 5 shows distal balloon catheter end portion 92 having inner surface friction member 98 and outer surface friction member 99 located interiorly and exteriorly of guide member 95, respectively.

Inner surface friction member 98 shown in FIG. 5 is adapted to increase the friction between the distal balloon catheter end portion 92 and a polymeric delivery shaft, which may be desired to help hold the balloon in a chosen position during in-vivo use. Positioning and repositioning of balloon 93 along a polymeric delivery shaft may be achieved according to the methods discussed relative to FIGS. 3A–B and using sufficient axial forces to break the static friction between inner surface friction member 98 and the polymeric delivery catheter shaft.

FIG. 5 also shows guide member 95 extending beyond the balloon tubing seal in a similar construction to the embodiment of FIG. 4. However, on the outer surface of this extended portion in FIG. 5 is an outer surface friction member 99, as opposed to the guide member outer surface threads 69. In this configuration, a positioner (not shown) may have a positioner cuff adapted with an inner diameter that may be advanced over the proximal extension of guide member 95 to coaxially engage outer surface friction member 99. Such engagement may allow for axial or rotational movement of distal balloon catheter end portion 92 via manipulation of the positioner as desired.

The material for inner surface friction member 98 or outer surface friction member 99 in FIG. 5 should be chosen for optimal frictional interface with either a delivery shaft or a positioner cuff, respectively. Such optimal interface would allow for controlled positioning during normal in-vivo use, together with the ability controllably to overcome the static friction of such interface during use, and slideably reposition the distal balloon catheter end portion along a delivery shaft or to disengage it from the positioner. Such material may be a separate polymeric tubular member that may be either heat shrunk, solvent bonded, or adhesive bonded to the distal balloon catheter end portion 92. Or, such material may be a high friction coating, such as a tacky polyurethane or silicone adhesive.

FIG. 6 shows an alternative positioner embodiment for use in a balloon/delivery catheter assembly of the invention. In this variation, positioner 100 is shown to have a tubular shaft rather than an isolated positioner cuff of the previously described embodiments. Positioner 100 is shown in FIG. 6, for purposes of example, together with the balloon/delivery catheter assembly 1 of FIG. 1.

In the embodiment of FIG. 6, positioner 100 has a longitudinal positioner shaft 102 with a positioner lumen 103 that runs the length of positioner 100 and is coaxial with delivery shaft 11. Positioner 100 is further shown to have a proximal positioner hub 104. Positioner hub 104 may be adapted to accommodate the mechanical strain due to manual manipulation and also may comprise a hemostatic valve or other type of seal mechanism for maintaining hemostasis through the interlumenal space surrounding the delivery catheter.

The coaxial, tubular construction of positioner 100 in FIG. 6 may provide several advantages. First, where significant push forces are required for axially moving the distal balloon catheter end portion 22, such a coaxially coupled arrangement may allow for higher force transmission and less prolapse than a "wire-and-cuff" design as described for other embodiments. Secondly, the wall forms a significantly larger torque radius in this arrangement than would be the case with a typical core wire. Therefore, where the material construction for such tubular positioner 100 is designed to optimize torque transmission, this may be a desirable configuration when rotation of the positioner is needed, such as for rotational positioning of the distal balloon catheter end portion in a balloon/delivery catheter assembly (such as assembly 2 of FIG. 4).

The construction of positioner 100 in FIG. 6 may be polymeric or of composite design. Such polymer may be polyethylene, polyurethane, NYLON(s), or other similarly extrudable materials, or additionally may comprise polyimide or polyamide. A wire reinforced or braided member may also be necessary in a composite with such polymers, for instance to achieve some level of desired torque transmission.

FIGS. 7A–C further shows another positioner embodiment that provides for alternative balloon repositioning mechanisms in the balloon/delivery catheter assembly embodiments just described. In FIGS. 7A–C, positioner 130 is shown to have a similar construction to the positioner 30 of FIG. 1 and is shown here with balloon/delivery catheter assembly 1 (as in FIG. 1). However, FIGS. 7A–C show the positioner cuff 132 to have a sufficient lumenal diameter to slide over not only the delivery shaft 11, but to also be coaxially positionable over balloon 23 of the distal balloon catheter end portion 22.

When positioner 130 is coaxially positioned over the deflated balloon 23, subsequent inflation of the balloon 23 engages the positioner cuff 132, as is shown in FIG. 7B. Such inflation preferably would be with sufficient force such that the distal balloon catheter end portion 22 may then be manipulated by manipulation of the positioner 130. After balloon inflation and engagement of positioner 130, distal balloon catheter end portion 22 may then be repositioned with axial movement of the positioner. FIG. 7C shows such repositioning, wherein positioner wire 134 is pulled to withdraw the distal balloon catheter end portion 22 along the delivery shaft 11. Similarly, such positioner/balloon engagement as just described and shown in FIGS. 7A–C allows for rotational movement of the distal balloon catheter end portion 22 and repositioning of the balloon 23.

Figure 8A:
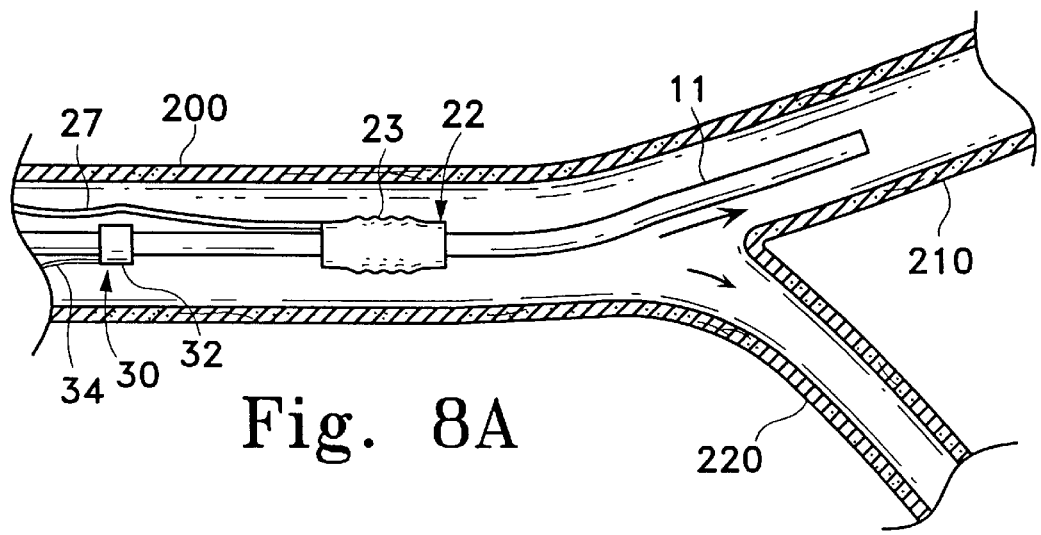
FIG. 8A shows a perspective view of an initial step in a method for using the inventive device, wherein a flow-directable delivery catheter is shown to be flow-directed into a first vessel of a bifurcation.
Figure 8B:
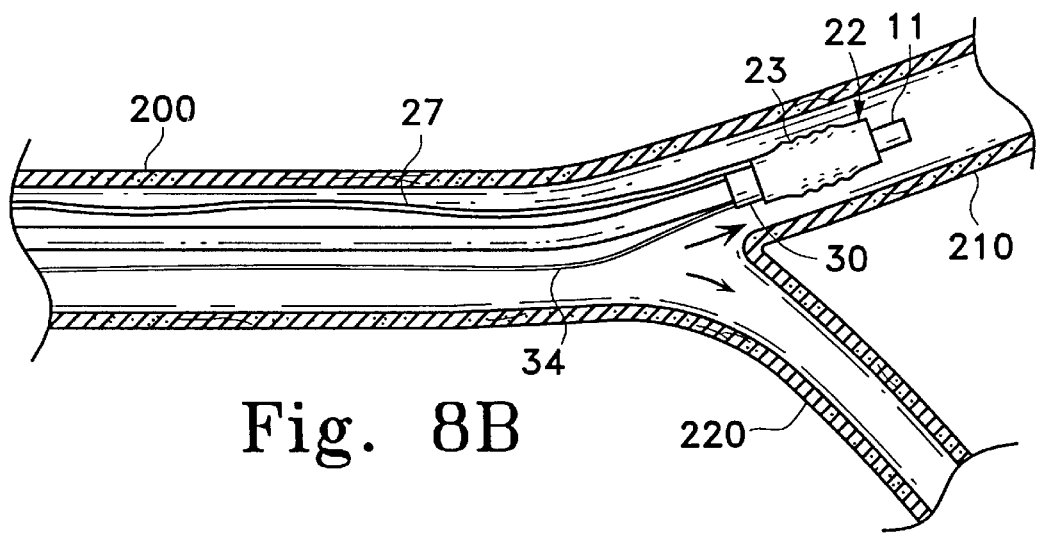
FIG. 8B shows a following step in the procedure of FIG. 8A, showing the balloon advanced over the delivery catheter and into the first vessel by the positioner.
Figure 8C:
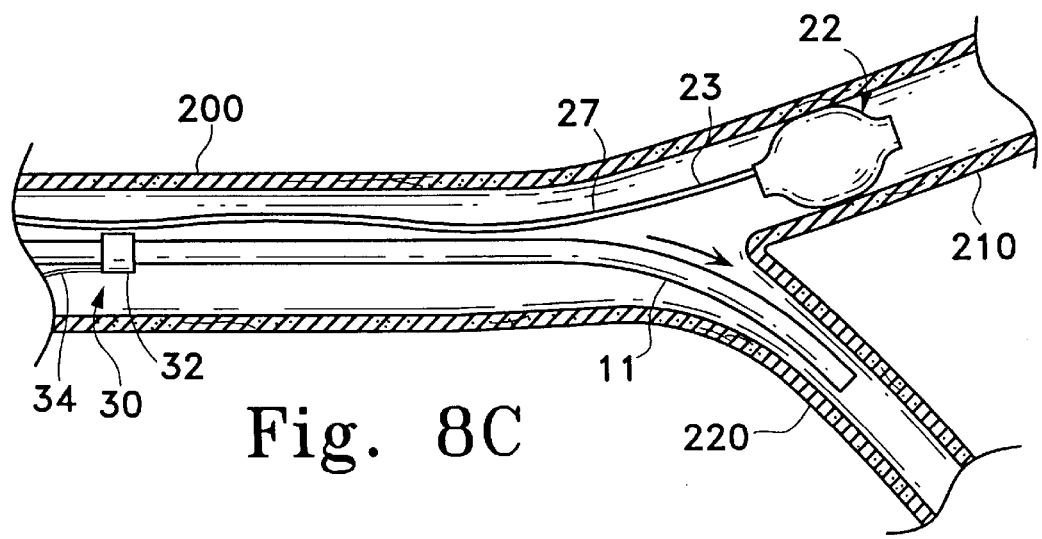
FIG. 8C shows a further step in the procedure of FIGS. 8A and 8B, showing the flow-directable delivery catheter withdrawn from the balloon catheter lumen, the balloon expanded to occlude flow into the first vessel, and the flow-directable delivery catheter advanced in the direction of increased flow into a second vessel.

FIGS. 8A–C show a preferred method of use of the previously described balloon/delivery catheter assembly embodiments, such as assemblies 1 and 2 in FIGS. 1 and 4, respectively. These embodiments comprise a balloon catheter having a distal balloon catheter end portion 22 coaxially positioned along a polymeric delivery shaft 11. The balloon catheters described also have an inflation shaft 27 proximal of the distal balloon catheter end portion 22 with a longitudinal axis that is out of alignment with the delivery shaft axis, the inflation shaft not being coaxially disposed about the delivery shaft. These features are shown in the progressive steps of FIGS. 8A–C to provide the ability to redirect a flow-directable delivery catheter 11 from a relatively "high-flow" branch and into a relatively "low-flow" branch at a vessel bifurcation. Such a use of balloon/delivery catheter assembly 1, such as that shown in FIG. 1, is shown in FIGS. 8A–C for purposes of example.

FIG. 8A shows balloon/delivery catheter assembly 1, including positioner 30, positioned in-vivo in a branching vessel bifurcation of feeding vessel 200. The distal tip of delivery shaft 11 is shown to be directed by physiological flow into a relatively "high-flow" branch 210 of the bifurcation, as would normally be the case with flow-directable delivery catheters. Distal balloon catheter end portion 22 is shown to be positioned such that balloon 23 is in a first position along the delivery shaft 11, which in FIG. 8A is shown to be proximally of the bifurcation and in the feeding vessel 200. Positioner 30 is shown in FIG. 8A with positioner cuff 32 coaxial to delivery shaft 11 and proximally of distal balloon catheter end portion 22.

FIG. 8B shows distal advancement of positioner 30 to reposition distal balloon catheter end portion 22 distally along delivery shaft 11 such that balloon 23 is in a second position on the delivery shaft 11. The second position is here shown in FIG. 8B to be distally beyond the bifurcation and within the relatively "high-flow" branch 210.

FIG. 8C shows balloon 23 in an inflated, expanded state in relatively "high-flow" branch 210, wherein flow into "high-flow" branch 210 is occluded and diverted to an elevated rate of flow in what was otherwise relatively "low-flow" branch 220. Positioner 30 is shown to be proximally withdrawn along delivery shaft 11 and back into feeding vessel 200. Polymeric delivery shaft 11 is shown in FIG. 8C after it has been withdrawn proximally from the now occluded, relatively "high-flow" branch 210 and into the feeding vessel 200, and then subsequently advanced again distally to follow the elevated flow into otherwise relatively "low-flow" branch 220.

In a similar procedure to that shown and described for FIGS. 8A–C, the balloon may be advanced distally of the delivery catheter in a first lumen, after which the delivery catheter may be withdrawn into the feeding vessel. Subsequent inflation of the balloon would occlude the first lumen. Infusion of agents through the delivery catheter thereafter would then be isolated from that first vessel. This method of using the novel assembly may be desirable when a first, occluded vessel leads to good tissue and other vessels branching from the proximal feeding vessel lead to diseased tissue requiring drug treatment or otherwise are the target of local agent infusion.

Figure 9A:
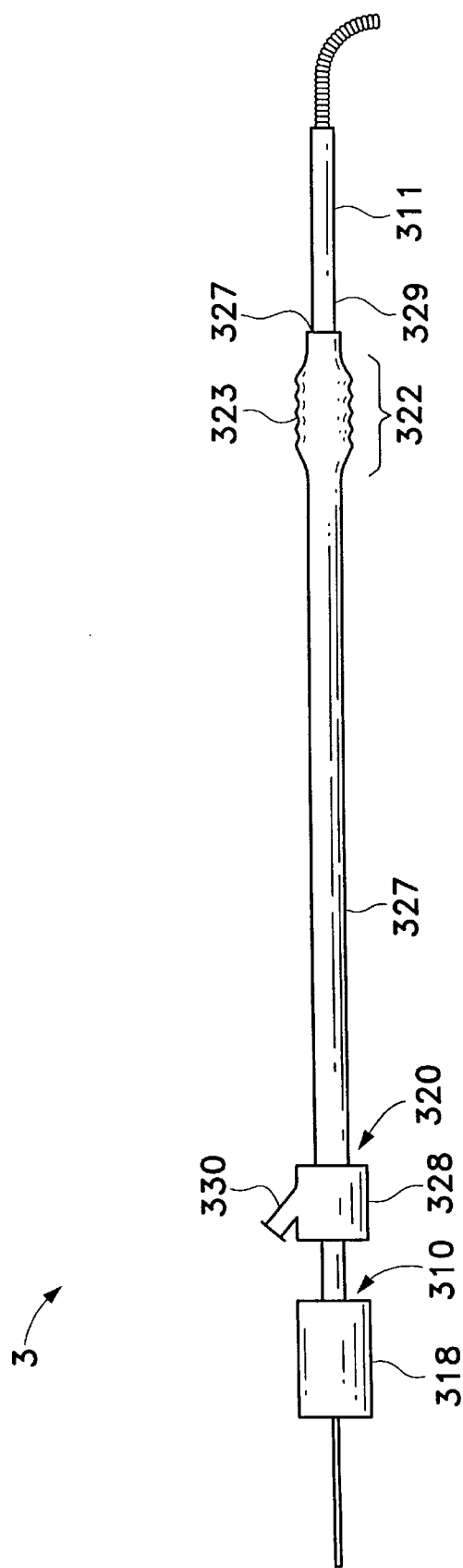
FIG. 9A shows a perspective view of another balloon/delivery catheter assembly of the invention, showing an inflation shaft of a balloon catheter, in addition to a distal balloon catheter end portion, in coaxial arrangement with a polymeric delivery catheter shaft.

FIG. 9A shows another variation of the invention: shown as balloon/delivery catheter assembly 3. Balloon/delivery catheter assembly 3 is shown in FIG. 9A to comprise a balloon catheter 320 having an inflation shaft 327, in addition to a distal balloon catheter end portion 322, both of which are coaxial to the polymeric delivery shaft 311.

The assembly of FIG. 9A obviates the need for a positioner, such as positioner 30 in FIG. 1, when balloon 323 is to be repositioned along the delivery shaft 311 while the assembly 3 is in the body. In this instance, the entire balloon catheter 320, including inflation shaft 327 which is proximally accessible to a physician during use, is coaxially slideable along the delivery catheter shaft. Using conventional delivery catheter designs, however, such coaxial positioning is limited within the natural confines of the assembly as a system. For instance, balloon catheter 320 may be coaxially slideable proximally along delivery shaft 311 only, up until the inflation coupler 328 meets the proximal delivery catheter coupler 318. This limits the proximal placement of the balloon along the delivery shaft. This embodiment may have an increased profile and stiffness when compared to the earlier discussed variations. Such trade-offs as these may be apparent when choosing the optimum variation of the invention for a particular intended use or anatomy.

Figure 9B:
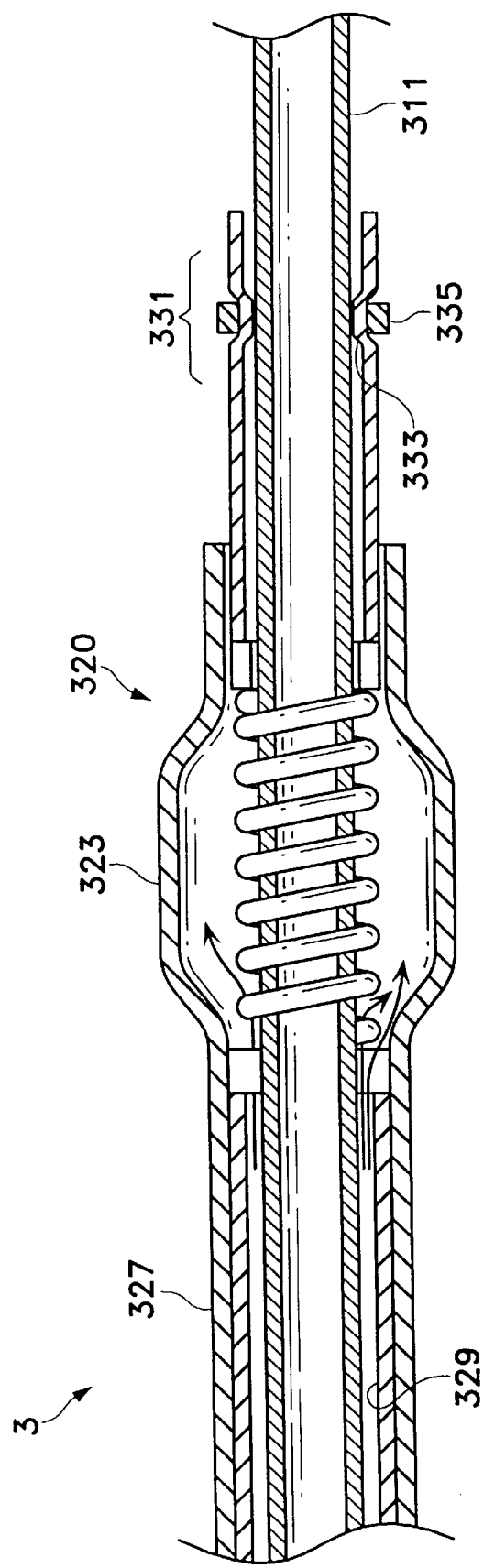
FIG. 9B shows a cut-away side view of the assembly of FIG. 9A, showing the balloon catheter as one preferred single-lumen design coaxially disposed about a polymeric delivery catheter shaft.

FIG. 9B shows assembly 3 of FIG. 9A in a more detailed cross-sectional view, wherein balloon catheter 320 is shown as a "single-lumen" type of balloon catheter. Inflation shaft 327 is shown to provide an inflation lumen 329 that fluidly couples inflation coupler 328 (not shown in FIG. 9B but shown in FIG. 9A) with expandable balloon 323 which is shown to be in an expanded state. A portion of delivery shaft 311 is shown to be coaxially housed within inflation lumen 329, and is shown extending coaxially under balloon 323, and distally through balloon catheter tip region 331.

In the balloon catheter tip region 331 is a valve seat 333, which is shown in FIG. 9B to be formed underneath a radiopaque tip marker 335. This valve seat 333 is designed to have a tight valve clearance with the outer diameter of delivery shaft 311. This valve clearance forms an interference fit with delivery shaft 311, although such interference fit preferably allows delivery shaft 311 to still be slideable therethrough when axial forces are applied for repositioning of the balloon 323 along the delivery shaft 311. Additionally, the clearance between valve seat 333 and delivery shaft 311 forms a barrier to distal fluid flow from the interior space of balloon 323, such that the balloon may be controllably inflated at elevated pressures.

Preferably, balloon 323 is expandable at low pressures and the valve clearance is such that air may escape under such pressures but the more viscous inflation media is at least substantially blocked from flowing therethrough. In addition, inflation coupler 328 (not shown in FIG. 9B but shown in FIG. 9A) preferably comprises an adjustable seal around delivery shaft 311 to provide a barrier to proximal fluid flow during balloon inflation. For instance, a conventional type of rotating hemostatic valve mechanism may be provided at the inflation coupler 328.

The design shown for balloon catheter 320 in FIG. 9B is similar to that disclosed in U.S. Pat. No. 5,304,198 to Samson, although modified as is herein described for use in the balloon/delivery catheter assembly of the current invention. The preferred material construction for such a design may also be similar to that disclosed in the Samson reference. The disclosure of that document is herein incorporated in its entirety by reference thereto.

Figure 10:
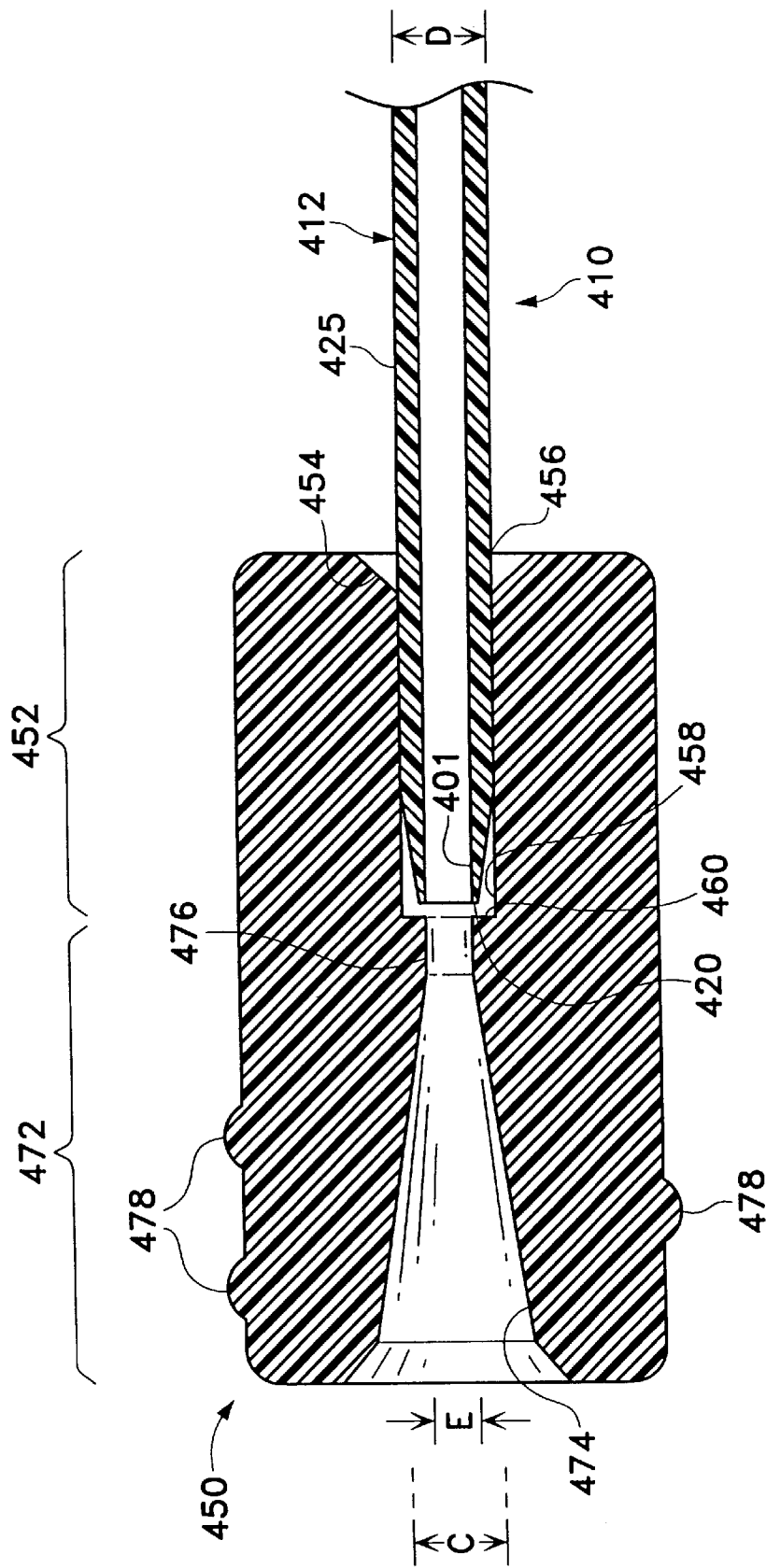
FIG. 10 shows a cut-away side view of a further polymeric delivery catheter embodiment, wherein a removable proximal delivery coupler is shown to be removably engaged with the polymeric delivery shaft.

FIG. 10 shows a further polymeric delivery catheter embodiment for use in the various balloon/delivery catheter assemblies herein described. FIG. 10 shows delivery catheter 410 as having a removable proximal delivery coupler 450. Removable proximal delivery coupler 450 is shown in FIG. 10 to be removeably coupled to proximal delivery shaft end portion 412.

For purposes of example, the removable coupler embodiments disclosed in pending U.S. patent application Ser. No. 08/522,746, filed Aug. 31, 1995, may be used as for the removable proximal delivery coupler 450. The disclosure of that document is herein incorporated by reference. FIG. 10 shows one such design for removable delivery coupler 450 in a sectional view. Coupler 450 is shown to preferably have two adjacent regions. The first coupler region 452 is a polymeric delivery shaft receiving region, and the second coupler region 472 is a second device receiving region.

As shown in FIG. 10, the first coupler region 452 includes a small funnel 454 for first encountering a polymeric delivery shaft and then directing it into the coupler. This is shown in FIG. 10 (by example) as funneling end 420 and polymeric delivery shaft end portion 412 into an elongated coupler lumen 456 having an inner diameter "C". The diameter "C" is limited in that polymeric delivery shaft end portion 412 must be removably fixed within coupler 450 by means of the engaging contact between polymeric delivery shaft outer surface 425 and coupler lumen inner surface 458.

In one embodiment, coupler 450 may be made of relatively elastic material, such as polyurethane, polyisoprene, polyvinyl chloride, styrene butadiene copolymer, low density polyethylene, a rubber such as silicone rubber, or blends thereof. In such a case, the coupler lumen 456 inner diameter "C" may be equal to or less than polymeric delivery shaft outer diameter "D". The ratio of these diameters, however, must allow for polymeric delivery shaft end portion 412 to be pressed into lumen 456 and up to stop 460, yet still allow for sufficient elastic force from the displaced lumen inner surface 458 to hold polymeric delivery shaft end portion 412 in removable engagement. The dimensions required for the two diameters "C" and "D" and the necessary corresponding ratio for meeting this performance requirement may vary depending on the materials chosen.

In another embodiment the coupler may be made of relatively inelastic material, such as polycarbonate, polyacrylate, mid to high density polyethylene, or blends thereof. Or, the inelastic material of the coupler may be a metal. When such an inelastic material is used, such a press fit as just described is not achievable without affecting the cross-section of the lumen of the polymeric delivery shaft contained therein, especially for example when the polymeric delivery shaft is a simple extruded tube of relatively yieldable material. Desirably, an inelastic coupler would be dimensioned such that diameter "C" is equal to or slightly larger than "D". In this embodiment, polymeric delivery shaft end portion 412 may be inserted into coupler lumen 456 and be removably engaged therein by friction between the polymeric delivery shaft outer surface 425 and coupler lumen surface 458.

Another alternative embodiment of the current invention contemplates the removable coupler having an adjustable inner diameter. In this embodiment, the catheter end portion receiving portion of the coupler has a first inner diameter and is adapted to slidably receive the polymeric delivery shaft end portion therein. Once the polymeric delivery shaft end portion is so placed within the coupler, the coupler inner diameter is adjusted down onto the outer surface of the polymeric delivery shaft with a force to hold it therein. Such an adjustable inner diameter may be achieved for example through the use of a collet or an O-ring, together with a compressing member as may be contemplated by one of ordinary skill.

The second coupler region 472 of FIG. 10, or the second device receiving region, is preferably adapted for receiving a device such as a pusher or guidewire, and is preferably so adapted by incorporating a large funnel as is shown at 474. Large funnel 474 is adapted to receive a pusher or guide wire or other object device and direct the device into the elongate body lumen 410 at polymeric delivery shaft end portion 412 located within first coupler region 452. The large funnel 474 has a first large funnel end 476 that is adjacent the first coupler region 452 and forms stop 460 for elongate body end portion 412. Large funnel end 476 has an inner diameter "E" that closely approximates the diameter of elongate body lumen 10 when body end portion 412 is removably engaged within first coupler region 452.

Thus, a relatively continuous surface is internally formed within coupler 450 when polymeric delivery shaft end portion 412 is advanced into first region lumen 456 and against the adjacent large funnel end 416. This facilitates a relatively smooth introduction of an object device into elongate body lumen 401 within the preferred coupler 450. Alternatively, large funnel end 476 may be designed with an inner diameter "E" that is slightly smaller than the diameter of lumen 401. In this configuration, introduction of object devices into lumen 401 through coupler 450 is further insured against a possibility of encountering a ridge at the elongate body end such as at 420. Additionally, this configuration may provide an additional stop to prevent passage of a device from lumen 401 proximally through coupler 450. For instance, a pre-loaded implant (not shown) in lumen 410 may be more safely housed therein when large funnel end 476 has inner diameter "E" smaller than the diameter of lumen 401.

Second coupler region 472 may also comprise a luer fitting that has threads for threadably engaging a coupler of a second device. The luer fitting can be either the male or female side of the two device adaption, and can have either outward threads, as shown at 478 in FIG. 10, or may be inwardly beveled to accept outward threads of a mating device. Additionally or alternatively, large funnel 474 may also be adapted to frictionally engage a discharge end of a syringe as may be apparent to one of ordinary skill.

In use of the embodiment of FIG. 10, the delivery catheter 410 may be introduced into the body and advanced to a desired site in the body independently of a balloon catheter (not shown) and before an assembly is formed with the balloon catheter. If it is desired to then position an expandable balloon along the in-dwelling delivery catheter 410, removable proximal delivery coupler 450 may then be removed from the delivery catheter 410, and the balloon catheter may thereafter be coaxially advanced over the polymeric delivery shaft 411 until the balloon is at the chosen position. The removable proximal delivery coupler 450 may then be replaced onto polymeric delivery shaft 411.

In forming a balloon/delivery catheter assembly with delivery catheter 410 of FIG. 10, any of the various balloon catheter embodiments herein described may suffice, as may be apparent to one of ordinary skill. For example, a particular embodiment for balloon catheter 420 may be chosen such that inflation shaft 427 is not coaxial with polymeric delivery shaft 411 (such as balloon catheter 20 of FIG. 1). In such a case, a positioner as provided in this disclosure may also be advanced over the polymeric delivery shaft 411 when removable proximal delivery catheter coupler 418 is removed. Further, a balloon may be at a first chosen position along polymeric delivery shaft 411 and removable proximal delivery coupler 450 may thereafter be removed in order to assemble the positioner with the polymeric delivery shaft 411. This allows for remote repositioning of the balloon to a second chosen position while the assembly remains disposed in-vivo.

Methods of Using the Invention

In general use of the current invention in the vascular system, standard vascular access techniques may be employed as would be apparent to one of ordinary skill. In brief, a desired access site in a vessel is punctured with a needle. A wire is then advanced through an internal bore of the needle and into the vessel, after which the needle is withdrawn off of the wire. A dilator is then advanced over the wire to dilate open the puncture site to a desired diameter such that an introducer sheath may be left across the dilated puncture site. The introducer sheath thereafter provides a conduit for introducing subsequent devices into the vasculature, such as for introducing the various embodiments of the current invention which may be advanced to a desired in-vivo site for treatment or diagnosis.

Medical procedures may benefit from the various balloon/delivery catheter assembly embodiments of the current invention because a physician may choose a desired, customized position along a polymeric delivery catheter shaft at which an expandable balloon may be placed. Such choosing may be based upon many variables surrounding the intended procedure, such as patient-dependent anatomical needs, anomalies of a particular disease state, or the desired treatment application itself. The balloon may be so positioned prior to insertion of the assembly through the introducer sheath, or after the delivery catheter is already positioned at a desired site in the body.

The balloon may be subsequently repositioned from a first chosen position to a second chosen position along the polymeric delivery shaft, depending upon a particular need and using methods as previously described with the particular embodiments. As previously described, this repositioning may be manually with the assembly withdrawn ex-vivo, or may be done remotely with the assembly remaining in-dwelling. Methods of use for remote repositioning the balloon along the delivery shaft may require steps wherein the assembly having the balloon in the first position is withdrawn into proximal, straight vasculature before repositioning is attempted. This is because the axial forces of repositioning the balloon along the polymeric delivery shaft may be difficult to transmit and may result in increased trauma within the more distal, tortuous soft tissues. For example, it may be required in a particular procedure to withdraw the assembly into the more straight vasculature in the neck region for balloon repositioning when performing procedures in the brain.

When the delivery catheter of the inventive assembly is an "over-the-wire" catheter, the vascular access methods as just described may further include coaxial tracking of the delivery catheter or the balloon/delivery catheter assembly over a guidewire. For example, a guidewire must be inserted into the body and generally will be advanced into a desired body space. Such advancement will generally involve pushing the wire forward, under X-ray guidance, while torqueing a proximal portion of the wire to cause a like rotation of a pre-shaped tip. Such tip-shape rotation may be used to sub-select branches of the anatomy, such as throughout the dividing tree of the vasculature. Finally, once the guidewire has been advanced to the remote in-vivo target site, the delivery catheter or balloon/delivery catheter assembly may be advanced over the guidewire.

Alternatively, when the delivery catheter of choice is a flow-directable catheter, the balloon/delivery catheter assembly may be directed into a target site by advancing the delivery catheter along the direction that the highly flexible delivery catheter tip region naturally takes when under physiological flow forces.

There are also several novel medical procedures that may be performed with the assembly embodiments. Among such procedures are re-directing "flow-directed" delivery catheters into physiologically "low-flow" vessels at branching locations, temporarily occluding vessels or bracing the delivery catheter positioning during isolated delivery of agents through delivery catheters, and dilating vessel stenoses.

One treatment method using the variably positionable balloon/delivery catheter assembly is for resisting delivery catheter recoil during delivery of agents through a port thereof. Such method involves expanding the balloon at a chosen location on the delivery catheter shaft prior to or while delivering a treatment or diagnostic agent through a lumen of the delivery catheter, out a port of the delivery catheter, and into a target body space. In order to increase support to the delivery catheter during delivery using this method, the balloon expansion would preferably be of such extent to exert a force against the tissue wall in order to thereby anchor the assembly.

Balloon inflation at a chosen position along the delivery shaft may also desirably occlude flow between regions of the body space surrounding the delivery catheter shaft and adjacent the balloon. Such occlusion may not necessarily engage the vessel wall when a complete occlusion is not required and when vessel wall trauma due to balloon inflation may be a concern. This type of use may be desired for isolating the delivery of agents from regions adjacent the balloon. Or, such inflation may be desired to divert flow for directing a flow directable delivery catheter as shown in FIGS. 8A–C and described in the accompanying text.

Balloon dilatation of a stenotic region of a vessel, such as in balloon angioplasty or fallopian tube dilatation, is an additional medical procedure that may benefit from the ability to expand a balloon at a chosen position along a polymeric delivery catheter shaft. In such a procedure, after the balloon is positioned at a chosen location along to the polymeric delivery shaft, the assembly may be advanced into a distal vascular site, preferably over a guidewire. The balloon may then be advanced across a stenotic region in the vessel and be expanded to dilate the stenosis. The customized placement of the balloon along the delivery catheter shaft in such a procedure may allow for the delivery of agents through the delivery catheter lumen at a desired distance distally from the balloon during balloon inflation, as a particular case may warrant. Or, such positioning may improve the transitions along the assembly for tracking throughout the tortuous vasculature in reaching a distal treatment site.

The foregoing specification provides detailed embodiments of the balloon/delivery catheter assembly of the current invention. However, such detailed descriptions should not be construed to unduly limit the scope of the invention. Combinations of the embodiments and improvements thereof that would be apparent to one of ordinary skill are contemplated as falling within the scope of the invention, which is defined by the following claims.

We claim as our invention:

1. A method of treating an internal body space of a patient with a balloon/delivery catheter assembly comprising the steps of:

inserting a polymeric delivery shaft of a delivery catheter, said delivery catheter including a distal delivery port fluidly coupled to a proximal coupler, into the body;

advancing the polymeric delivery shaft into an internal body space;

choosing a first position along the polymeric delivery shaft to place an expandable balloon of a distal balloon catheter end portion of a balloon catheter;

advancing a positioner coaxially over at least a portion of said polymeric delivery shaft to engage said distal balloon catheter end portion; and further advancing said positioner to advance the distal balloon catheter end portion coaxially along the polymeric delivery shaft until the expandable balloon is located at the first position.

2. The method of claim 1, wherein the distal balloon catheter end portion is coaxially advanced along the polymeric delivery shaft and the expandable balloon is located at the first position prior to inserting the polymeric delivery shaft into the body.

3. The method of claim 1, further comprising the prior steps of:

inserting a guidewire into the body;

advancing the guidewire into an internal body space; and coaxially advancing the polymeric delivery shaft over the guidewire.

4. The method of claim 1, further comprising the subsequent steps of:
- expanding the balloon; and
- delivering a treatment or diagnostic agent out the distal delivery port of the delivery catheter.

5. The method of claim 1, further comprising the steps of:
- advancing the balloon across a stenotic region in the internal body space; and
- expanding the balloon within the stenotic region.

6. The method of claim 1, further comprising the step of repositioning the distal balloon catheter end portion until the balloon is located at a second position along the polymeric delivery shaft.

7. The method of claim 6, further comprising the steps of:
- withdrawing the delivery catheter with the balloon in the first position from the body;
- manually moving the distal balloon catheter end portion along the polymeric delivery shaft until the balloon is located at the second position; and
- reinserting the delivery catheter, with the balloon located at the second position, into the body.

8. A method of treating an internal body space of a patient with a balloon/delivery catheter assembly comprising the steps of:
- inserting a polymeric delivery shaft of a delivery catheter, said delivery catheter including a distal delivery port that is fluidly coupled to a proximal coupler, into the body;
- advancing the polymeric delivery shaft into an internal body space;
- choosing a first position along the polymeric delivery shaft to place an expandable balloon of a distal balloon catheter end portion of a balloon catheter;
- advancing the distal balloon catheter end portion coaxially along the polymeric delivery shaft until the expandable balloon is located at the first position;
- repositioning the distal balloon catheter end portion until the balloon is located at a second position along the polymeric delivery shaft; and
- applying axial force to the distal balloon catheter end portion sufficient to move the distal balloon catheter end portion axially along the polymeric delivery shaft.

9. A method of treating an internal body space of a patient with a balloon/delivery catheter assembly comprising the steps of:
- inserting a polymeric delivery shaft of a delivery catheter, said delivery catheter including a distal delivery port that is fluidly coupled to a proximal coupler, into the body;
- advancing the polymeric delivery shaft into an internal body space;
- choosing a first position along the polymeric delivery shaft to place an expandable balloon of a distal balloon catheter end portion;
- advancing the distal balloon catheter end portion coaxially along the polymeric delivery shaft until the expandable balloon is located at the first position threadably coupling said distal balloon catheter end portion and said delivery catheter; advancing a positioner coaxially over at least a portion of said polymeric delivery shaft to engage said distal balloon catheter end portion;
- repositioning the distal balloon catheter end portion until the balloon is located at a second position along the polymeric delivery shaft; by rotating one of either the distal balloon catheter or end position delivery catheter relative to the other.

10. A method of treating an internal body space of a patient with a balloon/delivery catheter assembly comprising the steps of:
- inserting a polymeric delivery shaft of a delivery catheter, said delivery catheter including a distal delivery port that is fluidly coupled to a proximal coupler, into the body;
- advancing the polymeric delivery shaft into an internal body space;
- choosing a first position along the polymeric delivery shaft to place an expandable balloon of a distal balloon catheter end portion of a balloon catheter;
- advancing the distal balloon catheter end portion coaxially along the polymeric delivery shaft until the expandable balloon is located at the first position;
- repositioning the distal balloon catheter end portion until the balloon is located at a second position along the polymeric delivery shaft;
- coaxially advancing a positioner cuff of a positioner distally along the polymeric delivery shaft to engage the distal balloon catheter end portion; and
- applying force to a proximal portion of the positioner extending outside the body sufficient to cause movement of the distal balloon catheter end portion relative to the polymeric delivery shaft.

11. The method of claim 10, further comprising the steps of:
- advancing the positioner cuff coaxially over the balloon; and
- expanding the balloon to engage the positioner cuff with the distal balloon catheter end position.

12. A method of treating an internal body space of a patient with a balloon/delivery catheter assembly comprising the steps of:
- inserting a polymeric delivery shaft of a delivery catheter, said delivery catheter including a distal delivery port that is fluidly coupled to a proximal coupler, into the body;
- advancing the polymeric delivery shaft into an internal body space;
- choosing a first position along the polymeric delivery shaft to place an expandable balloon of a distal balloon catheter end portion of a balloon catheter, wherein the balloon catheter further comprises an inflation shaft;
- advancing the distal balloon catheter end portion coaxially along the polymeric delivery shaft until the expandable balloon is located at the first position;
- repositioning the distal balloon catheter end portion until the balloon is located at a second position along the polymeric delivery shaft; and
- applying tension to the inflation shaft sufficient to cause movement of the distal balloon catheter end portion relative to the polymeric delivery shaft.

13. A method of treating an internal body space of a patient with a balloon/delivery catheter assembly comprising the steps of:
- inserting a polymeric delivery shaft of a delivery catheter, said delivery catheter including a distal delivery port that is fluidly coupled to a proximal coupler, into the body;
- advancing the polymeric delivery shaft into an internal body space;

choosing a first position along the polymeric delivery shaft to place an expandable balloon of a distal balloon catheter end portion of a balloon catheter;

advancing the distal balloon catheter end portion coaxially along the polymeric delivery shaft until the expandable balloon is located at the first position;

removing a proximal delivery coupler from the polymeric delivery shaft; and coaxially sliding the distal balloon catheter end portion over the polymeric delivery shaft.

14. A method of treating an internal body space of a patient with a balloon/delivery catheter assembly comprising the steps of:

inserting a polymeric delivery shaft of a delivery catheter, said delivery catheter including a distal delivery port that is fluidly coupled to a proximal coupler, into the body, wherein the polymeric delivery shaft is flow-directable;

advancing the polymeric delivery shaft into an internal body space;

choosing a first position along the polymeric delivery shaft to place an expandable balloon of a distal balloon catheter end portion of a balloon catheter;

advancing the distal balloon catheter end portion coaxially along the polymeric delivery shaft until the expandable balloon is located at the first position;

placing the polymeric delivery shaft into a first branch vessel extending distally from of a feeding vessel;

advancing a positioner distally along the polymeric delivery shaft until it engages the distal balloon catheter end portion;

advancing the distal balloon catheter end portion with the positioner distally beyond the polymeric delivery shaft;

withdrawing the positioner proximally along the polymeric delivery shaft;

withdrawing the polymeric delivery shaft proximally into the feeding vessel;

expanding the balloon to occlude flow in the first branch vessel; and advancing the polymeric delivery shaft into a second branch vessel extending from the feeding vessel.

* * * * *